US008637089B2

(12) United States Patent
Zhang et al.

(10) Patent No.: US 8,637,089 B2
(45) Date of Patent: *Jan. 28, 2014

(54) MICRONIZED WOOD PRESERVATIVE FORMULATIONS

(75) Inventors: Jun Zhang, Getzville, NY (US); Robert M. Leach, Grand Island, NY (US)

(73) Assignee: Osmose, Inc., Buffalo, NY (US)

( * ) Notice: Subject to any disclaimer, the term of this patent is extended or adjusted under 35 U.S.C. 154(b) by 337 days.

This patent is subject to a terminal disclaimer.

(21) Appl. No.: 11/526,765

(22) Filed: Sep. 26, 2006

(65) Prior Publication Data

US 2007/0193473 A1    Aug. 23, 2007

Related U.S. Application Data

(63) Continuation-in-part of application No. 10/821,326, filed on Apr. 9, 2004, now Pat. No. 7,674,481, and a continuation-in-part of application No. 10/970,446, filed on Oct. 21, 2004.

(60) Provisional application No. 60/461,547, filed on Apr. 9, 2003, provisional application No. 60/518,994, filed on Nov. 11, 2003, provisional application No. 60/568,485, filed on May 6, 2004.

(51) Int. Cl.
*A01N 59/00* (2006.01)
*A01N 59/20* (2006.01)

(52) U.S. Cl.
USPC .............................. 424/630; 424/633; 424/634

(58) Field of Classification Search
USPC .......................................... 424/630, 633, 634
See application file for complete search history.

(56) References Cited

U.S. PATENT DOCUMENTS

| | | |
|---|---|---|
| 1,388,513 A | 8/1921 | Chandler |
| 1,999,458 A | 4/1935 | Hollister |
| 2,892,261 A | 6/1959 | Hutchinson |
| 3,007,844 A | 11/1961 | Schulz |
| 3,231,464 A | 1/1966 | Dettwiler et al. |
| 3,321,464 A | 5/1967 | Soboczenski et al. |
| 3,443,881 A | 5/1969 | Hudson |
| 3,535,423 A | 10/1970 | Ordas |
| 3,622,377 A | 11/1971 | Conner |
| 3,816,307 A | 6/1974 | Woods |
| 3,837,875 A | 9/1974 | Murphy |
| 3,945,834 A | 3/1976 | Clarke et al. |
| 3,945,835 A | 3/1976 | Clarke et al. |
| 3,957,494 A | 5/1976 | Oberley |
| 3,968,276 A | 7/1976 | Allen |
| 4,003,994 A | 1/1977 | Downer et al. |
| 4,028,218 A * | 6/1977 | Fink et al. ..................... 516/118 |
| 4,058,607 A | 11/1977 | Hennart et al. |
| 4,061,770 A | 12/1977 | Marks |
| 4,062,991 A | 12/1977 | Kyte et al. |
| 4,067,862 A | 1/1978 | Crosby |
| 4,075,325 A | 2/1978 | Kauzal |
| 4,075,326 A | 2/1978 | Kuyama et al. |
| 4,142,009 A | 2/1979 | Kyte et al. |
| 4,172,904 A | 10/1979 | Young et al. |
| 4,310,590 A | 1/1982 | Petigara |
| 4,313,976 A | 2/1982 | Leach |
| 4,339,617 A | 7/1982 | Imai et al. |
| 4,404,169 A | 9/1983 | Ploss et al. |
| 4,507,152 A | 3/1985 | Collins et al. |
| 4,622,248 A | 11/1986 | Leach et al. |
| 4,626,544 A * | 12/1986 | Schulz et al. ................. 514/383 |
| RE32,329 E | 1/1987 | Paszner |
| 4,649,065 A | 3/1987 | Hein et al. |
| 4,657,789 A | 4/1987 | Lars |
| 4,663,364 A * | 5/1987 | Iwasaki et al. ................ 514/476 |
| 4,670,430 A | 6/1987 | Imamura et al. |
| 4,737,491 A | 4/1988 | Leppavuori et al. |
| 4,741,971 A | 5/1988 | Beck et al. |
| 4,778,833 A | 10/1988 | Van der Drift et al. |
| 4,779,735 A | 10/1988 | Kelso, Jr. |
| 4,783,221 A | 11/1988 | Grove |
| 4,808,406 A | 2/1989 | Brinkman |
| 4,857,322 A | 8/1989 | Goettsche et al. |
| 4,857,365 A | 8/1989 | Hirao et al. |
| 4,894,262 A | 1/1990 | Heitmanek |

(Continued)

FOREIGN PATENT DOCUMENTS

| | | |
|---|---|---|
| AU | 646732 | 10/1992 |
| AU | B-15117/92 | 10/1992 |

(Continued)

OTHER PUBLICATIONS

Aikin et al. Metallurgical Transactions, Nov. 1993, vol. 24A, p. 2465.*

(Continued)

*Primary Examiner* — Janet Epps-Smith
*Assistant Examiner* — Courtney Brown
(74) *Attorney, Agent, or Firm* — Covington & Burling LLP; Einar Stole; Melody Wu

(57) ABSTRACT

The present invention provides wood preservative compositions comprising micronized particles. In one embodiment, the composition comprises dispersions of micronized metal or metal compounds. In another embodiment, the wood preservative composition comprises an inorganic biocide comprising a metal or metal compound and organic biocide. When the composition comprises an inorganic biocide and an organic biocide, the inorganic biocide or the organic biocide or both are present as micronized particles. When compositions of the present invention are used for preservation of wood, there is minimal leaching of the metal and biocide from the wood.

14 Claims, 7 Drawing Sheets

(56) References Cited

U.S. PATENT DOCUMENTS

| | | | |
|---|---|---|---|
| 4,897,427 A | 1/1990 | Barnavon et al. | |
| 4,923,894 A | 5/1990 | Kanda et al. | |
| 4,988,545 A | 1/1991 | Laks | |
| 5,049,677 A | 9/1991 | Prout et al. | |
| 5,145,684 A | 9/1992 | Liversidge et al. | |
| 5,147,686 A | 9/1992 | Ichimura et al. | |
| 5,169,883 A | 12/1992 | Rainer | |
| 5,186,947 A | 2/1993 | Goettsche et al. | |
| 5,187,194 A | 2/1993 | Goettsche et al. | |
| 5,187,200 A | 2/1993 | Rainer | |
| 5,196,407 A | 3/1993 | Goletz et al. | |
| 5,200,421 A | 4/1993 | Ludwig et al. | |
| 5,207,823 A | 5/1993 | Shiozawa | |
| 5,234,747 A | 8/1993 | Walser et al. | |
| 5,248,450 A | 9/1993 | Metzner et al. | |
| 5,277,979 A | 1/1994 | Kielbania, Jr. et al. | |
| 5,304,376 A | 4/1994 | Friedrichs et al. | |
| 5,342,438 A | 8/1994 | West | |
| 5,346,943 A | 9/1994 | Khungar et al. | |
| 5,360,783 A | 11/1994 | Itoh et al. | |
| 5,397,795 A | 3/1995 | Valcke | |
| 5,405,705 A | 4/1995 | Fujimoto et al. | |
| 5,424,077 A | 6/1995 | Lajoie | |
| 5,426,121 A | 6/1995 | Bell | |
| 5,438,034 A * | 8/1995 | Walker | 504/158 |
| 5,461,726 A | 10/1995 | Walker | |
| 5,462,589 A | 10/1995 | Nicholas et al. | |
| 5,462,931 A | 10/1995 | Shaber et al. | |
| 5,484,934 A * | 1/1996 | Ikeda et al. | 548/213 |
| 5,492,681 A | 2/1996 | Pasek et al. | |
| 5,527,384 A | 6/1996 | Williams et al. | |
| 5,527,423 A | 6/1996 | Neville et al. | |
| 5,527,816 A | 6/1996 | Shaber et al. | |
| 5,536,305 A | 7/1996 | Yu | |
| 5,552,378 A | 9/1996 | Trinh et al. | |
| 5,624,916 A | 4/1997 | Shaber et al. | |
| 5,634,967 A | 6/1997 | Williams et al. | |
| 5,635,217 A | 6/1997 | Goettsche et al. | |
| 5,667,795 A | 9/1997 | Fraley et al. | |
| 5,700,841 A | 12/1997 | Walker | |
| 5,714,507 A | 2/1998 | Valcke et al. | |
| 5,747,519 A | 5/1998 | Kodama et al. | |
| 5,763,364 A | 6/1998 | Frisch et al. | |
| 5,777,110 A | 7/1998 | Davis et al. | |
| 5,804,591 A | 9/1998 | Valcke et al. | |
| 5,817,369 A | 10/1998 | Conradie et al. | |
| 5,833,741 A | 11/1998 | Walker | |
| 5,853,766 A | 12/1998 | Goettsche et al. | |
| 5,855,817 A | 1/1999 | Walker | |
| 5,874,025 A * | 2/1999 | Heuer et al. | 252/383 |
| 5,874,456 A | 2/1999 | McDade | |
| 5,874,476 A | 2/1999 | Hsu et al. | |
| 5,879,025 A * | 3/1999 | Blumenthal | 280/741 |
| 5,891,921 A | 4/1999 | Walker | |
| 5,916,356 A | 6/1999 | Williams et al. | |
| 5,972,266 A | 10/1999 | Fookes et al. | |
| 5,990,043 A | 11/1999 | Kugler et al. | |
| 6,033,648 A | 3/2000 | Candau | |
| 6,074,986 A | 6/2000 | Mulqueen et al. | |
| 6,087,303 A | 7/2000 | Walker | |
| RE36,798 E | 8/2000 | Williams et al. | |
| 6,110,263 A | 8/2000 | Goettsche et al. | |
| 6,123,756 A | 9/2000 | Poppen et al. | |
| 6,139,879 A | 10/2000 | Taylor | |
| 6,250,350 B1 | 6/2001 | Muraki et al. | |
| 6,274,199 B1 | 8/2001 | Preston et al. | |
| 6,303,183 B1 | 10/2001 | Wilczynski et al. | |
| 6,306,201 B1 | 10/2001 | Makino | |
| 6,306,202 B1 | 10/2001 | West | |
| 6,340,384 B1 | 1/2002 | Walker | |
| 6,352,583 B1 | 3/2002 | Goettsche et al. | |
| 6,372,297 B1 | 4/2002 | Davis et al. | |
| 6,372,771 B1 | 4/2002 | Ludwig et al. | |
| 6,448,279 B1 | 9/2002 | Tseng et al. | |
| 6,482,814 B1 * | 11/2002 | Bath et al. | 514/184 |
| 6,485,790 B2 | 11/2002 | Walker et al. | |
| 6,503,306 B1 | 1/2003 | Watkins | |
| 6,514,512 B1 | 2/2003 | Puterka et al. | |
| 6,521,288 B2 | 2/2003 | Laks et al. | |
| 6,527,981 B1 | 3/2003 | Tseng et al. | |
| 6,541,038 B1 | 4/2003 | Tanaka et al. | |
| 6,558,685 B1 | 5/2003 | Kober et al. | |
| 6,572,788 B2 | 6/2003 | Walker | |
| 6,576,661 B1 | 6/2003 | Bruck et al. | |
| 6,579,354 B1 | 6/2003 | West | |
| 6,585,989 B2 | 7/2003 | Herbst et al. | |
| 6,596,246 B2 | 7/2003 | Huato et al. | |
| 6,620,349 B1 | 9/2003 | Lopez | |
| 6,646,147 B2 | 11/2003 | Richardson et al. | |
| 6,689,854 B2 | 2/2004 | Fan et al. | |
| 6,699,818 B1 | 3/2004 | Walter et al. | |
| 6,753,035 B2 | 6/2004 | Laks et al. | |
| 6,843,837 B2 | 1/2005 | Zhang et al. | |
| 6,849,276 B1 | 2/2005 | Dufau et al. | |
| 6,905,531 B2 | 6/2005 | Richardson et al. | |
| 6,905,532 B2 | 6/2005 | Richardson et al. | |
| 7,105,136 B2 * | 9/2006 | Ploss et al. | 423/23 |
| 7,238,654 B2 | 7/2007 | Hodge et al. | |
| 7,252,706 B2 | 8/2007 | Richardson et al. | |
| 7,316,738 B2 | 1/2008 | Richardson et al. | |
| 7,426,948 B2 | 9/2008 | Richardson et al. | |
| 7,449,130 B2 | 11/2008 | Lloyd et al. | |
| 2001/0021711 A1 | 9/2001 | Beilfuss et al. | |
| 2001/0051175 A1 | 12/2001 | Strom et al. | |
| 2002/0003179 A1 | 1/2002 | Verhoff et al. | |
| 2002/0047058 A1 | 4/2002 | Verhoff et al. | |
| 2002/0051892 A1 * | 5/2002 | Laks et al. | 428/541 |
| 2002/0055046 A1 | 5/2002 | Ono et al. | |
| 2002/0128367 A1 | 9/2002 | Daisey et al. | |
| 2003/0013799 A1 | 1/2003 | Crooks et al. | |
| 2003/0026942 A1 | 2/2003 | Hejna et al. | |
| 2003/0040569 A1 | 2/2003 | Curry et al. | |
| 2003/0060504 A1 | 3/2003 | Yoshida et al. | |
| 2003/0077219 A1 | 4/2003 | Ploss et al. | |
| 2003/0108759 A1 | 6/2003 | Roos et al. | |
| 2003/0127023 A1 | 7/2003 | Grandidier et al. | |
| 2004/0024099 A1 | 2/2004 | Narayanan et al. | |
| 2004/0050298 A1 | 3/2004 | Giger et al. | |
| 2004/0051084 A1 | 3/2004 | Wessling et al. | |
| 2004/0063847 A1 | 4/2004 | Curry et al. | |
| 2004/0176477 A1 | 9/2004 | Davison et al. | |
| 2004/0258766 A1 | 12/2004 | Lemaire | |
| 2004/0258767 A1 | 12/2004 | Leach et al. | |
| 2004/0258768 A1 | 12/2004 | Richardson et al. | |
| 2004/0258838 A1 | 12/2004 | Richardson et al. | |
| 2005/0013939 A1 | 1/2005 | Vinden et al. | |
| 2005/0107467 A1 | 5/2005 | Richardson | |
| 2005/0118280 A1 | 6/2005 | Leach et al. | |
| 2005/0130866 A1 | 6/2005 | Richardson et al. | |
| 2005/0152994 A1 | 7/2005 | Leach et al. | |
| 2005/0182152 A1 | 8/2005 | Nonninger et al. | |
| 2005/0249812 A1 | 11/2005 | Leach et al. | |
| 2005/0252408 A1 | 11/2005 | Richardson et al. | |
| 2005/0255251 A1 | 11/2005 | Hodge et al. | |
| 2005/0256026 A1 | 11/2005 | Hodge et al. | |
| 2005/0265893 A1 | 12/2005 | Leach et al. | |
| 2006/0062926 A1 | 3/2006 | Richardson et al. | |
| 2006/0075921 A1 | 4/2006 | Richardson et al. | |
| 2006/0075923 A1 | 4/2006 | Richardson | |
| 2006/0078686 A1 | 4/2006 | Hodge et al. | |
| 2006/0086284 A1 | 4/2006 | Zhang et al. | |
| 2006/0086841 A1 | 4/2006 | Richardson et al. | |
| 2006/0112850 A1 | 6/2006 | Zhang et al. | |
| 2006/0147632 A1 | 7/2006 | Zhang et al. | |
| 2006/0217447 A1 | 9/2006 | Blow | |
| 2006/0257578 A1 | 11/2006 | Zhang et al. | |
| 2006/0276468 A1 | 12/2006 | Blow | |
| 2006/0288904 A1 | 12/2006 | Leach et al. | |
| 2007/0021385 A1 | 1/2007 | Zhang et al. | |
| 2007/0131136 A1 | 6/2007 | Zhang et al. | |
| 2007/0193473 A1 | 8/2007 | Zhang et al. | |
| 2007/0259016 A1 | 11/2007 | Hodge et al. | |
| 2008/0199525 A1 | 8/2008 | Leach et al. | |
| 2008/0199535 A1 | 8/2008 | Taylor et al. | |

(56) References Cited

U.S. PATENT DOCUMENTS

| | | |
|---|---|---|
| 2008/0210121 A1 | 9/2008 | Zhang et al. |
| 2008/0213608 A1 | 9/2008 | Richardson et al. |
| 2008/0260841 A1 | 10/2008 | Leach et al. |
| 2008/0286380 A1 | 11/2008 | Zhang et al. |
| 2009/0028917 A1 | 1/2009 | Leach et al. |
| 2009/0035564 A1 | 2/2009 | Leach et al. |
| 2009/0092683 A1 | 4/2009 | Leach et al. |
| 2009/0280185 A1 | 11/2009 | Richardson et al. |

FOREIGN PATENT DOCUMENTS

| | | |
|---|---|---|
| AU | 199723934 | 10/1997 |
| CA | 2103470 | 8/1994 |
| CA | 2103470 A1 | 8/1994 |
| CA | 2251534 | 10/1997 |
| CA | 2251534 A1 | 10/1997 |
| CA | 2321353 | 3/2001 |
| CA | 2400425 | 8/2001 |
| DE | 1531868 | 11/1978 |
| DE | 1531868 U | 11/1978 |
| DE | 41 12 652 | 10/1992 |
| DE | 4112652 | 10/1992 |
| DE | 4112652 A1 | 10/1992 |
| EP | 0 472 973 | 3/1992 |
| EP | 0472973 | 3/1992 |
| EP | 0472973 A1 | 3/1992 |
| EP | 0511541 | 11/1992 |
| EP | 0641164 | 3/1995 |
| EP | 0715625 | 6/1996 |
| EP | 1018413 | 7/2000 |
| EP | 1 034 903 | 9/2000 |
| EP | 1034903 | 9/2000 |
| EP | 1034903 A1 | 9/2000 |
| GB | 222268 | 10/1924 |
| GB | 222268 A | 10/1924 |
| GB | 491330 | 8/1938 |
| GB | 812408 | 4/1959 |
| GB | 812408 A | 4/1959 |
| GB | 822869 | 11/1959 |
| GB | 822869 A | 11/1959 |
| GB | 1 491 330 | 11/1977 |
| GB | 1491330 A | 11/1977 |
| JP | 60-155403 | 8/1985 |
| JP | 60-155403 A | 8/1985 |
| JP | 61-244502 A | 10/1986 |
| JP | S61-244052 | 10/1986 |
| JP | S61-244502 | 10/1986 |
| JP | S61-246002 | 11/1986 |
| JP | S61-246002 A | 11/1986 |
| JP | S61246002 | * 11/1986 |
| JP | S62-39201 | 2/1987 |
| JP | S62-116102 | 5/1987 |
| JP | 10-26401 | 1/1989 |
| JP | 10-26401 A | 1/1989 |
| JP | 03-047102 | 2/1991 |
| JP | 07309701 | 11/1995 |
| JP | 8-039511 | 2/1996 |
| JP | 8-183010 | 7/1996 |
| JP | 8-183010 A | 7/1996 |
| JP | 10-272610 | 10/1998 |
| JP | 10-272610 A | 10/1998 |
| JP | 11-207706 | 8/1999 |
| JP | 2000-102907 | 4/2000 |
| JP | 2000-102907 A | 4/2000 |
| JP | 2000-141316 A | 5/2000 |
| JP | 2000141316 | 5/2000 |
| JP | 2000141316 A | * 5/2000 |
| JP | 2001002514 | 1/2001 |
| JP | 2001-121512 A | 5/2001 |
| JP | 2001121512 | 5/2001 |
| JP | 2001-121512 | 8/2001 |
| JP | 2001279917 | 10/2001 |
| NZ | 225428 | 3/1991 |
| NZ | 225428 A | 3/1991 |
| NZ | 280716 | 2/1999 |
| NZ | 280716 A | 2/1999 |
| NZ | 304884 | 3/1999 |
| NZ | 304884 A | 3/1999 |
| RU | 642166 | 1/1979 |
| RU | 2166254 | 5/2001 |
| SE | 379167 | 9/1975 |
| SE | 379167 B | 9/1975 |
| SU | 642166 A1 | 1/1979 |
| WO | 85/00040 | 1/1985 |
| WO | WO-85/00040 A1 | 1/1985 |
| WO | WO 8500040 | 1/1985 |
| WO | 92/19429 | 11/1992 |
| WO | WO-92/19429 A1 | 11/1992 |
| WO | 95/27600 | 10/1995 |
| WO | WO-95/27600 A1 | 10/1995 |
| WO | WO 9818328 | 5/1998 |
| WO | 9955505 | 11/1999 |
| WO | WO-99/55505 A1 | 11/1999 |
| WO | 00/05955 | 2/2000 |
| WO | WO-00/05955 A1 | 2/2000 |
| WO | 00/24259 | 5/2000 |
| WO | 00/24528 | 5/2000 |
| WO | WO-00/24259 A1 | 5/2000 |
| WO | WO-00/24528 A1 | 5/2000 |
| WO | WO 0024259 | 5/2000 |
| WO | WO 0024528 | 5/2000 |
| WO | 00/78281 | 12/2000 |
| WO | WO-00/78281 A1 | 12/2000 |
| WO | WO 0078281 | 12/2000 |
| WO | 01/91925 | 12/2001 |
| WO | WO-01/91925 A1 | 12/2001 |
| WO | WO 0191925 | 12/2001 |
| WO | 02/06417 | 1/2002 |
| WO | WO-02/06417 A1 | 1/2002 |
| WO | WO 0213605 | 2/2002 |
| WO | 03/103392 | 12/2003 |
| WO | WO 03/103392 | 12/2003 |
| WO | WO-03/103392 A1 | 12/2003 |
| WO | 2004/091875 | 10/2004 |
| WO | WO-2004/091875 A2 | 10/2004 |
| WO | WO 2005098135 | 10/2005 |
| WO | 2006044218 | 4/2006 |
| WO | WO-2006/044218 A2 | 4/2006 |

OTHER PUBLICATIONS

AJ Panshin, et al., Textbook of Wood Technology, 4th ed. pp. 112-113 (1980).

American Wood-preservers' Association Standard E10-01 (2003), pp. 1-11.

American Wood-preservers' Association Standard E11-97 (2003), pp. 1-3.

American Wood-preservers' Association Standard E7-01 (2003), pp. 1-9.

Hawley's Condensed Chemical Dictionary, 14th edition, John Wiley & Sons, Inc. 2001, p. 86.

International Society of Soil Science, (http://clays.org.au/mins.htm).

Douglas J. Gardner, et al.; Wood Composite Protection, American Chemical Society, Symposium Series, 2003, pp. 399-419, Chapter 25, USA.

H.J. Deppe, Examination of the Protective Treatment of Plywood, Bundesantst, Mater., 1986, p. 333-340, vol. 44(9), Hoiz als Roh-und Werkstoff, Berlin-Dahlem, Germany.

Lide, "Characteristics of particles and particle dispersoids" handbook of chemistry and physics, 75th edition, 1994, Florida, CRC press, p. 15-38.

Liu Y, "Use of polymer nanopartcles as carriers for the controlled release of biocides in solid wood" Ph.D. dissertation of Yong Liu, Michigan Technological University, Houghton, MI.

Liu, Y. et al. "Use of nanoparticles for controlled release of biocides in solid wood" journal of applied polymer science, vol. 79, 2001, pp. 458-465.

Liu, Y. et al., Michigan Technical Univ. Dept. Chemistry, Houghton, MI, "Use of Polymeric Nanoparticles for controlled release of biocides in solid wood" Materials research society symposium proceedings series, 1998, vol. 550, abstract GG3.4.

(56) References Cited

OTHER PUBLICATIONS

Superior Court of New Jersey Chancery Division, Final Judgment, *Phibrotech, Inc.* v. *Osmose Holdings, Inc. Osmose, Inc.* Aug. 14, 2007.
Superior Court of New Jersey, Decision after trial, *Phibrotech Inc.* v. *Osmose Holdings, Inc.*, Jun. 25, 2007.
Survey of American Termites and Corresponding Measures for Preservation and Treatment, Mar. 1998.
American Wood-Preservers' Association Standard C1-03 (2003).
Backman P. A. et al., The Effects of Particle Size and Distribution on Performance of the Fungicide Chlorothalonil, Phytopathology, St. Paul, MN, US, vol. 66, No. 10, Jan. 1, 1976, pp. 1242-1245, XP009062911.
AWPA Standard E7-01.
AWPA Standard E10-01.
The Merck Index (12th Ed. 1996) Merck & Co., Inc.
Davis, Food Storage and Preservative-Treated Wood, Alaska Science Forum (Mar. 10, 1980) [online] [retrieve on Nov. 10, 2008]. URL:http://www.gi.alaska.edu/Science Forum/ASF3/380.htm/.
STN online, file SCISEARCH, Acc. No. 1993:540390 (Siegfried, Comparative Toxicity of Pyrethroid Insecticides to Terrestrial and Aquatic Insects, Environmental Toxicology and Chemistry (1993), vol. 12, No. 9, pp. 1683-1689), Abstract.
"A New Approach to Non-Toxic, Wide-Spectrum, Ground-Contact Wood Preservatives, Part I. Approach and Reaction Mechanisms," Holzforschung vol. 47, No. 3, 1993, pp. 253-260.
American Wood Preservers' Association (AWPA) Standard E10-1, 2005.
American Wood Preservers' Association (AWPA) Standard E7-01, 2006.
American Wood Preservers' Association (AWPA) Standard E-11-97 (2003), pp. 1-3.
Backman, P.A. et al., The Effects of Particle Size and Distribution on Performance of the Fungicide Chlorothalonil, Phytopathology, St. Paul, MN, US, vol. 66, No. 10, Jan. 1, 1976, pp. 1242-1245, XP009062911.
Barnes, H. M., et al., The Impact of Test Site and Oil Content on the Performance of Pentachlorophenol-treated Wood, Forest Products Journal, vol. 56, No. 5, pp. 43-47, May 2006.
Borkow, Gadi, et al., Copper as a Biocidal Tool, Proceedings, Ninety-Fifth Annual Meeting of the American Wood-Preservers' Association, vol. 95, May 16-19, 1999.
Crusberg, T.C., et al., Biomineralization of Heavy Metals, pp. 409-417, 2004.
Cui, F. and Archer, K. J., "Treatment of lumbar with preservative/water repellent emulsions—The significance of shear stability on penetration," The International Research Group on Wood Preservation, IRG/WP 97-20124, Paper prepared for the 28th Annual Meeting, Whistler, British Columbia, Canada (May 25-30, 1997).
Davis, Food Storage and Preservative-Treated Wood, Alaska Science Forum (Mar. 10, 1980) [online] [retrieve on Nov. 10, 2008]. URL: http://www.gi.alaska.edu/Science Forum/ASF3/380.htm/.
Feist and Mraz, Forest Products Lab Madison Wis., Wood Finishing: Water Repellents and Water-Repellent Preservatives. Revision, Report No.-FSRN-FPL-0124-Rev (NTIS 1978).
Fojutowski, A.; Lewandowski, O., Zesz. Probl. Postepow Nauk Roln. No. 209: 197-204 (1978).
Hamilton, R. L. and Cosse, O. K., "Thermal Conductivity of Heterogenous Two-Component Systems," Ind. & Engr. Chem. Fund., 1, 187-191 (1962).
Hawley's Condensed Chemical Dictionary, 14th edition; John Wiley & Sons, Inc., 2001, p. 86.
Humar, M., et al., Changes of the pH of Impregnated Wood During Exposure to Wood-Rotting Fungi, Holz als Roh-und Werkstoff 59 (2001) 288-293.
Humar, M., et al., Effect of Oxalix, Acetic Acid, and Ammonia on Leaching of Cr and Cu from Preserved Wood, Wood Sci Technol 37 (2004) 463-473.
Humar, M., et al., Influence of Moisture Content on EPR Parameters of Copper in Impregnated Wood, Holz als Roh-und Werkstoff 59 (2001) 254-255.
International Society of Soil Science. (http://www.clays.org.au/mins.htm).
Kartal, S. N., et al., Do the Unique Properties of Nanometals Affect Leachability or Efficacy Against Fungi and Termines? International Biodeterioration & Biodegradation 63 (2009) 490-495.
Koch, C. C., Synthesis of Nanostructured Materials by Mechanical Milling: Problems and Opportunities, NanoStructured Materials, vol. 9, pp. 13-22, 1997.
Kubel, H., et al., The Chemistry and Kinetic Behaviour of Cu—Cr—As/B Wood Preservatives—Part 5. Reactions of CCB and Cellulose, Lignin and their Simple Model Compounds, Holzforschung und Holzverwertung 34 (1982) 4, pp. 75-83.
Lebow, Stan, et al., Fixation Effects on the Release of Copper, Chromium and Arsenic From CCA-C Treated Marine Piles, Report Prepared for American Wood-Preservers' Association Subcommittee P-3, Piles, Aug. 1999, pp. 168-174.
Lide; "Characteristics of Particles and Particle Dispersoids"; Handbook of Chemistry and Physics; 75th Edition; 1994; Florida: CRC Press, pp. 15-38.
Liu, Y., et al., "Use of Nanoparticles for the Controlled Release of Biocides in Pressure-Treated Solid Wood"; Presentation at American Chemical Society, Las Vegas, Oct. 1997.
Liu, Y., et al.; "Use of Nanoparticles for Controlled Release of Biocides in Solid Wood"; Journal of Applied Polymer Science, vol. 29, 2001, pp. 458-465.
Liu, Y., et al.; Michigan Technical Univ., Dept. of Chemistry, Houghton, MI; "Use of Polymeric Nanoparticles for Controlled Release of Biocides in Solid Wood"; Materials Research Society Symposium Proceedings Series; 1998; vol. 550, Abstract GG3.4.
Liu, Y., et al; "Use of Nanoparticles for the Controlled Release of Biocides in Pressure-Treated Solid Wood"; Polymer Preprints 38(2), 1997, pp. 624-625.
Liu, Y.; "Use of Polymer Nanoparticles as Carriers for the Controlled release of Biocides in Solid Wood"; Ph.D. Dissertation of Yong Liu; Michigan Technological University, Houghton, MI, 1999.
Morrell, J. J. Wood Pole Maintenance Manual (1996 Edition), Research Contribution 15, Oct. 1996, p. 22.
Nanotechnology in brief, Feb. 20, 2004, available at http://nanotechweb.org/articles/news/3/2/12/1.
Nasibulin, Albert G., Ahonen, P. Petri, Richard, Richard, Olivier, Esko I, "Copper and Copper Oxide Nanoparticle Formation by Chemical Vapor Nucleation From Copper (II) Acetylacetonate," Journal of Nanoparticle Research 3(5-6): 383-398 (2001).
Panshin AJ and De Zeeuw, Carl, Textbook of Wood Technology, 4th ed. pp. 112-113 (1980).
Pizzi, A., A New Approach to Non-Toxic, Wide Spectrum, Ground-Contact Wood Preservatives. Part II. Accelerated and Long-Term Field Tests, Holzforschung 47 (1993) 343-348.
Pizzi, A., et al., The Chemistry and Kinetic Behaviour of Cu—Cr—AS/B Wood Preservatives—Part 6. Fixation of CCB in Wood and Physical and Chemical Comparison of CCB and CCA, Holzforschung and Holzverwertung 34 (1982) 5, pp. 80-86.
Ratajczak, Izabela, et al., Fixation of Copper(II)-Protein Formulation in Wood: Part 1. Influence of Tannic Acid on Fixation of Copper in Wood, Holzforschung, vol. 62, pp. 294-299, 2008.
Rathore, H. S., et al., Fungicide and Herbicide Residues in Water, Handbook of Water Analysis, pp. 608-654, Handbook of Water Analysis, 2000.
Rech, Helmuth, Location of Pentachlorophenol by Electron Microscopy and Other Techniques in Cellon Treated Douglas-Fir, Forest Products J. 21/1, pp. 38-43, Jan. 1971.
S. E. A. McCallan, The Nature of the Fungicidal Action of Copper and Sulfur, The Botanical Review.
Schultz, T .P., et al., A Brief Overview of Non-Arsenical Wood Preservative, American Chemical Society, Chapter 26, pp. 420-429, 2003.
Shaw; www.fda.gov/ohrms/dockets/ac/01/slides/3763s2_09_shaw.ppt; 2001.
STN online, file SCISEARCH, Acc. No. 1993:540390 (Siegfried, Comparative Toxicity of Pyrethroid Insecticides to Terrestial and

(56) References Cited

OTHER PUBLICATIONS

Aquatic Insects, Environmental Toxicology and Chemistry (1993), vol. 12, No. 9, pp. 1683-1689), Abstract.
Superior Court of New Jersey Chancery Division, Final Judgment, *Phibro-Tech, Inc.* v. *Osmose Holdings, Inc., Osmose, Inc.*, Aug. 14, 2007.
Superior Court of New Jersey, Decision After Trial, *Phibro-Tech, Inc.* v. *Osmose Holding, Inc.*, Jun. 25, 2007.
Wapnir, Raul A., Copper Absorption and Bioavailability, Am J Clin Nutr 1998; 67 (suppl.): 1054S-60S.
The Merck Index (12th Ed. 1996) Merck & Co., Inc., pp. 1555-1556.
Thompson, R., CBE, The Chemistry of Wood Preservation, Feb. 28-Mar. 1, 1991.
Zahora, A. R. and Rector, C.M., "Water Repellent Additives for Pressure Treatments" Proceedings of the Eleventh Annual Meeting of the Canadian Wood Preservation Association, Toronto, Ontario, 11:22-41 (Nov. 6-7, 1990).
"Defendants' Answer to Plaintiff's Amended Complaint and Defendants' Counterclaims," *Osmose, Inc.* v. *Arch Chemicals, et al.*, USDC, Eastern District of VA, Norfolk Division Case No. C.A. No. 2:10 cv 108-JBF/FBS.
"Osmose's Answer to Defendants' Counterclaims," *Osmose, Inc.* v. *Arch Chemicals, et al.*, USDC, Eastern District of VA, Norfolk Division Case No. C.A. No. 2:10 cv 108-JBF/FBS.
Rudd, et al. "The Influence of Ultraviolet Illumination on the Passive Behavior of Zinc," Journal of the Electrochemical Society, 147 (4) p. 1401-1407, 2000.
Request for Inter Partes Reexamination of U.S. Appl. No. 7,674,481, filed by Arch Wood Protection, Inc. with the United States Patent and Trademark Office on Aug. 13, 2010 and a draft of the Request.
Bailey, Irving W., "The Preservative Treatment of Wood, II. The Structure of the Pit Membranes in the Tracheids of Conifers and their Relation to the Penetration of Gases, Liquids, and Finely Divided Solids into Green and Seasoned Wood," Forest Quarterly, 11:12-20, p. 15 (1913).
Merriam-Webster's Collegiate Dictionary, 10th ed., 1993.
Amended Notice of Opposition to Grant of Patent (Section 21) and Statement of Case (Application No. 542889) filed by Mattersmiths Holdings Limited on Aug. 23, 2010, Intellectual Property Office of New Zealand.
Proceedings of the Fourth International Congress of Pesticide Chemistry (IUPAC), Article VII-23, 1978.
Backman, P.A., et al., "The Effects of Particle Size and Distribution on Performance of the Fungicide Chlorothalonil," Disease Control and Pest Management, St. Paul, MN, vol. 66, No. 10, Jan. 1, 1976, pp. 1242-1245, XP009062911.
Supplementary European Search Report for PCT/US2005/016503 dated Feb. 2, 2009.
Supplementary European Search Report for PCT/US2005/037303 dated Feb. 5, 2009.
Koch, C.C., Synthesis of Nanostructured Materials by Mechanical Milling: Problems and Opportunities, NanoStructured Materials, vol. 9, pp. 13-22, 1997.
American Wood-Preservers' Association Standard E7-07, "Standard Method of Evaluating Preservatives by Filed Tests with Stakes," 2006.
American Wood-Preservers' Association Standard E10-01, "Standard Method of Testing Wood Preservatives by Laboratory Soil-Block Cultures," 2005.
The Merck Index (12th Ed. 1996) Merck & Co., Inc., pp. 9253-9254.
Davis, Food Storage and Preservative-Treated Wood, Alaska Science Forum (Mar. 10, 1980) [online] [retrieved on Nov. 10, 2008]. URL:http://www.gi.alaska.edu/ScienceForum/ASF3/380.htm/.
STN online, file SCISEARCH, Acc. No. 1993:540390 (Siegfried, Comparative Toxicity of Pyrethroid Insecticides to Terrestial and Aquatic Insects, Environmental Toxicology and Chemistry (1993)), vol. 12, No. 9, pp. 1683-1689.
Superior Court of New Jersey, Decision After Trial, *Phibro-Tech, Inc.* v. *Osmose Holdings, Inc.*, Jun. 25, 2007.
Superior Court of New Jersey, Chancery Division, Final Judgment, *Phibro-Tech, Inc.* v. *Osmose Holdings, Inc., Osmose, Inc.*, Aug. 14, 2007.
Liu, Y., et al., Use of Nanoparticles for the Controlled Release of Biocides in Pressure-Treated Solid Wood, Polymer Preprints 38(2), 1997, pp. 624-625.
Liu, Y., et al., Michigan Technological Univ., Dept. of Chemistry, Houghton, MI, Use of Polymeric Nanoparticles for Controlled Release of Biocides in Solid Wood, Materials Research Society Symposium Proceedings Series, 1998, vol. 550, Abstract GG3.4.
Liu, Y., "Use of Polymer Nanoparticles as Carriers for the Controlled release of Biocides in Solid Wood," Ph.D. Dissertation, Michigan Technological University, Houghton, MI, 1999.
Liu, Y., et al., Use of Nanoparticles for Controlled Release of Biocides in Solid Wood, Journal of Applied Polymer Science, vol. 79, 2001, pp. 458-465.
Lide, D., Ed., Characteristics of Particles and Particles Dispersoids, Handbook of Chemistry and Physics, 75th edition, 1994, Florida: CRC Press, p. 15-38.
Shaw, A.B., "Liposome Drug Products: Chemistry Manufacturing and Control Issues," (www.fda.gov/ohmrms/dockets/ac/01/slides/3763s2_09_shaw.ppt), 2001, 2 pages.
"About Clays," International Society of Soil Science. (http://www.clays.org.au/mins.htm) Nov. 22, 2006, 4 pages.
Hawley's Condensed Chemical Dictionary, 14th Edition, John Wiley & Son, Inc., 2001, p. 86.
First Office Action issued Oct. 21, 2010 in Inter Partes Reexamination Control No. 95/001,418.
Action closing Prosecution issued Apr. 29, 2011 in Inter Partes Reexamination Control No. 95/001,418.
Schultz, T.P., et al., "A Brief Overview of Non-Arsenical Wood Preservative," American Chemical Society, Chapter 26, pp. 420-429, 2003.
S. E. A. McCallan, The Nature of the Fungicidal Action of Copper and Sulfur, The Botanical Review, pp. 629-643, Aug. 30, 1948.
M. Humar et al., "Influence of Moisture Content on EPR Parameters of Copper in Impregnated Wood," Holz als Roh-und Werkstoff 59 (2001) 254-255.
M. Humar et al., "Changes of the pH of Impregnated Wood During Exposure to Wood-Rotting Fungi," Holz als Roh-und Werkstoff 59 (2001) 288-293.
A. Pizzi, "A New Approach to Non-Toxic, Wild-Spectrum, Ground-Contact Wood Preservatives. Part I. Approach and Reaction Mechanisms," Holzforschung 47 (1993) 253-260.
A. Pizzi, "A New Approach to Non-Toxic, Wild-Spectrum, Ground-Contact Wood Preservatives. Part II. Accelerated and Long-term Field Tests," Holzforschung 47 (1993) 343-348.
Stan Lebow, et al., "Fixation Effects on the Release of Copper, Chromium and Arsenic From CCA-C Treated Marine Piles, Report Prepared for American Wood-Preservers' Association Subcommittee P-3, Piles," Aug. 1999, pp. 168-174.
Izabela Ratajczak, et al., "Fixation of Copper (II)-Protein Formulation in Wood: Part 1. Influence of Tannic Acid on Fixation of Copper in Wood," Holzforschung, vol. 62, pp. 294-299, 2008.
S. N. Kartal, et al., "Do the Unique Properties of Nanometals Affect Leachability or Efficacy Against Fungi and Termites?" International Biodeterioration & Biodegradation 63 (2009) 490-495.
H. Kubel, et al., "The Chemistry and Kinetic Behavior of Cu—Cr—As/B Wood Preservatives—Part 5. Reactions of CCB and Cellulose, Lignin and their Simple Model Compounds," Holzforschung and Holzverwertung 34 (1982) 4, pp. 75-83.
A. Pizzi, et al., "The Chemistry and Kinetic Behavior of Cu—Cr—As/B Wood Preservatives—Part 6. Fixation of CCB in Wood and Physical and Chemical Comparison of CCB and CCA," Holzforschung and Holzverwertung 34 (1982) 5, pp. 80-86.
Raul A. Wapnir, Copper Absorption and Bioavailability, Am J Clin Nutr 1998; 67 (suppl.): 1054S-60S.
Gadi Borkow, et al., "Copper as a Biocidal Tool," Proceedings, Ninety-Fifth Annual Meeting of the American Wood-Preservers' Association, vol. 95, May 16-19, 1999.
H. S. Rathore, et al., "Fungicide and Herbicide Residues in Water," Handbook of Water Analysis, pp. 608-654, 2000.

(56) References Cited

OTHER PUBLICATIONS 5.1 Inorganic Fungicides—5.1.1 Metal Salts, Pesticide Chemistry, pp. 272-486, 1988.

R. Thompson, The Chemistry of Wood Preservation, Feb. 28-Mar. 1, 1991.

H. M. Barnes, et al., The Impact of Test Site and Oil Content on the Performance of Pentachlorophenol-Treated Wood, Forest Products Journal, vol. 56, No. 5, pp. 43-47, May 2006.

J.J. Morrell, Wood Pole Maintenance Manual (1996 Edition), Research Contribution 15, Oct. 1996, p. 22.

Helmuth Resch, "Location of Pentachlorophenol by Electron Microscopy and Other Techniques in Cellon Treated Douglas-Fir," Forest Products J. 21/1, pp. 38-43, Jan. 1971.

Cui, F. and Archer, K.J., "Treatment of lumber with preservative/water repellent emulsions—The significance of shear stability on penetration," The International Research Group on Wood Preservation, IRG/WP 97-20124, Paper prepared for the 28th Annual Meeting, Whistler, British Columbia, Canada (May 25-30, 1997).

Feist and Mraz, Forest Products Lab Madison Wis., Wood Finishing: Water Repellents and Water-Repellent Preservatives. Revision, Report No.-FSRN-FPL-0124-Rev ( )NTIS 1978.

Fojutowski, A., and Lewandowski, O., Zesz. Probl. Postepow Nauk Roln. No. 209: 197-204 (1978).

Hamilton, R.L. and Cosse, O.K., "Thermal Conductivity of Heterogeneous Two-Component Systems," Ind. & Engr. Chem. Fund., 1, 187-191 (1962).

Laks, et al., "Polymer Nanoparticles as a Carrier System for Wood Preservatives," PowerPoint Presentation to Rohm & Haas under confidentiality agreement, Oct. 30, 1998 (even-numbered pages not available).

"Nanotechnology in brief," Feb. 20, 2004, http://nanotechweb.org/articles/news/3/2/12/1.

Nasibulin, Albert G., et al., "Copper and Copper Oxide Nanoparticle Formation by Chemical Vapor Nucleation From Copper (II) Acetylacetonate," Journal of Nanoparticle Research 3(5-6): 383-398 (2001).

Panshin AJ and De Zeeuw, Carl, Textbook of Wood Technology, 4th ed., pp. 112-113 (1980).

Bailey, Irving W., "The Preservative Treatment of Wood, II. The Structure of the Pit Membranes in the Tracheids of Conifers and their Relation to the Penetration of Gases, Liquids, and Finely Divided Solids into Green and Seasoned Wood," Forest Quarterly, 11:12-20 p. 15 (1913).

Merriam-Webster's Collegiate Dictionary, 10th ed., 1993, p. 733.

The Copper Champs! Unique Copper Hydroxide Formulations (Brochure), Nufarm Americas Inc. (2002).

Zahora, A. R. and Rector, C.M., "Water Repellent Additives for Pressure Treatments," Proceedings of the Eleventh Annual Meeting of the Canadian Wood Preservation Association, Toronto, Ontario, 11:22-41 (Nov. 6-7, 1990).

"Defendants' Answer to Plaintiff's Amended Complaint and Defendants' Counterclaims," *Osmose, Inc.* v. *Arch Chemicals, et al.*, USDC, Eastern District of VA, Norfolk Division Case No. C.A. No. 2:10 cv 108-JBF/FBS Jun. 21, 2010.

"Osmose's Answer to Defendants' Counterclaims," *Osmose, Inc.* v. *Arch Chemicals, et al.*, USDC, Eastern District of VA, Norfolk Division Case No. C.A. No. 2:10 cv 108-JBF/FBS Jun. 21, 2010.

"Defendants' Supplemental Response to Interrogatory No. 12 and its Subparts," *Osmose, Inc.* v. *Arch Chemicals, et al.*, USDC, Eastern District of VA, Norfolk Division Case No. C.A. No. 2:10 cv 108-JBF Aug. 26, 2010.

Notice of Opposition to a European Patent (Application No. EP04776802.3/Patent No. EP1651401), filed by Dr. David Elsy on Apr. 21, 2010.

Statement of Grounds and Particulars filed by Arch Wood Protection Pty Ltd. with the Commissioner of Patents on Dec. 18, 2009, In the Matter of Australian Patent Application No. 2004230950 in the name of Osmose, Inc.

Rudd, et al. "The Influence of Ultraviolet Illumination on the Passive Behavior of Zinc," Journal of the Electrochemical Society, 147(4), p. 1401-1407, 2000.

American Wood-Preservers' Association (AWPA) Standard A3-00, 2003.

Proceedings of the Fourth International Congress Pesticide Chemistry (IUPAC), Article VII-23, 1978.

Statutory Declaration of Dr. Robin Nicholas Wakeling, in the matter of Australian Patent Acceptance No. 2004230950 and Opposition thereto, dated Sep. 20, 2010.

Hungarian Search Report dated Jul. 15, 2010 for Singaporean Patent Application No. 200717645-6.

Australian Patent Office Examination Report dated Jun. 1, 2010 for Singaporean Patent Application No. 200717652-2.

Notice of Opposition to Grant of Patent (Section 21) (Application No. 542889) filed by Mattersmiths Holdings Limited on Jun. 22, 2010.

Ernest W. Flick, "Fungicides, Biocides and Preservatives for Industrial and Agricultural Applications," 1987, Noyes Publication, p. 184.

American Wood-Preservers' Association (AWPA) Standard E-11-97, pp. 1-3, 2003.

Opinion and Order dated Jan. 28, 2011, *Osmose, Inc.* v. *Arch Chemicals, Inc., et al.*, Civil Action No. 2:10 cv 108.

Expert Report of Dr. Frank Beall, Ph.D. Concerning the Invalidity of U.S. Patent No. 7,674,481, U.S. District Court for the Eastern District of Virginia, Norfolk Division, Civil Action No. 2:10 cv 108 Jan. 21, 2011.

Supplemental Expert Report of Dr. Frank Beall, Ph.D. Concerning the Invalidity of U.S. Patent No. 7,674,481, Feb. 11, 2011, USDC Eastern District of Virginia, Norfolk Division, Civil Action No. 2:10cv108.

Rebuttal Expert Report of John Ruddick, USDC Eastern District of Virginia, Norfolk Division, Civil Action No. 2:10cv108 Feb. 22, 2010. (Redacted).

American Wood Preservers' Association (AWPA) Standard E10-06, "Standard Method of Testing Wood Preservatives by Laboratory Soil-Block Cultures," 2007.

American Wood Preservers' Association (AWPA) Standard E10-09, "Standard Method of Testing Wood Perseverative by Laboratory Soil-Block Cultures," 2010.

American Wood Preservers' Association (AWPA) Standard E11-06, "Standard Method of Determining the Leachability of Wood Preservatives," 2007.

American Wood Preservers' Association (AWPA) Standard E22-09, "Standard Accelerated Laboratory Method for Testing the Efficacy of Preservatives Against Wood Decay Fungi Using Compression Strength," 2010.

ASTM D5664, "Standard Test Method for Evaluating the Effects of Fire-Retardant Treatments and Elevated Temperatures on Strength Properties of Fire-Retardant Treated Lumber," 2002.

Freeman, Mike et al., "A Comprehensive Review of Copper-Based Wood Preservatives," Forest Products Journal, vol. 58, No. 11, pp. 6-27, Nov. 2008.

Stirling, Rod, et al., "Micro-Distribution of Micronized Copper in Southern Pine," The International Research Group on Wood Protection, 39th Annual Meeting, May 25-28, 2008.

The Federal Circuit Bar Association Model Patent Jury Instructions, Feb. 18, 2010.

Liese, W., "Fine Structure of Bordered Pits in Softwoods," Cellular Ultrastructure of Woody Plants, pp. 271-290, 1995.

Response to Office Action by Patent owner in Inter Partes Reexamination under 37 CFR § 1.945, USPTO Reexamination Control No. 95/001,418, filed by Osmose, Inc., Dec. 21, 2010.

Third Party Comments after Patent Owner Response, USTPO Reexamination Control No. 95/001,418, filed by Arch Wood Protection, Inc., Jan. 20, 2011.

Liu, Y., et al., "Use of Nanoparticles for the Controlled Release of Biocides in Pressure-treated Solid Wood," Presentation at the American Chemical Society, Las Vegas, Oct. 1997.

Amended Notice of Opposition to Grant of Patent (Section 21) and Statement of Case (Application No. 542889) filed by Mattersmiths Holdings Limited on Aug. 23, 2010; and Notice of Opposition to

(56) References Cited

OTHER PUBLICATIONS

Grant of Patent (Section 21) (Application No. 542889) filed by Mattersmiths Holdings Limited on Jun. 22, 2010.
Request for Inter Partes Reexamination of U.S. Patent No. 7,674,481 filed with the United States Patent and Trademark Office by Arch Wood Protection, Inc. on Aug. 13, 2010 and a draft of the Request.
Patent Owner's Response Under 37 CFR 1.951(a) to the Action Closing Prosecution in Inter Partes Reexamination Control No. 95/001,418. May 27, 2011.
Declaration of Dr. John N.R. Ruddick Under 37 CFR 1.132, in Inter Partes Reexamination Control No. 95/001,418. May 26, 2011.
Supplementary European Search Report dated Apr. 21, 2009 for PCT/US2005/035946.
Defendants' Supplemental Response to Interrogatory No. 12 and its Subparts dated Aug. 26, 2010, *Osmose, Inc.* v. *Arch Chemicals, et al.*, USDC Eastern District of VA, Norfolk Division, Case No. C.A. No. 2:10 cv 108-JBF.
"Fungicides, Biocides and Preservatives for Industrial and Agricultural Applications," by Ernest W. Flick, 1987, Noyes Publications, p. 184.
Opinion and Order, *Osmose, Inc.* v. *Arch Chemicals, Inc., et al.*, Jan. 28, 2011, USDC Eastern District of Virginia, Norfolk Division, Civil Action No. 2:10 cv 108.
Expert Report of Dr. Frank Beall, Ph.D. Concerning the Invalidity of U.S. Patent No. 7,674,481, USDC Eastern District of Virginia, Norfolk Division, Civil Action No. 2:10cv108, Jan. 21, 2011.
Rebuttal Expert Report of John Ruddick, USDC Eastern District of Virginia, Norfolk Division, Civil Action No. 2:10cv108, Feb. 22, 2011 (redacted).
American Wood Preservers' Association (AWPA) Standard E10-09, "Standard Method of Testing Wood Preservatives by Laboratory Soil-Block Cultures," 2010.
ASTM D5664, "Standard Test Method for Evaluating the Effects of Fire-Retardant Treatments and Elevated Temperatures on Strength Properties of Fire Retardant Treated Lumber," 2002.
Freeman, Mike H., et al., "A Comprehensive Review of Copper-Based Wood Preservatives," Forest Products Journal, vol. 58, No. 11, pp. 6-27, Nov. 2008.
The Federal Circuit Bar Association Model Patent Jury Instructions, last edited Feb. 18, 2010.
Liese, W., "Fine Structure of Bordered Pits in Softwoods, Cellular Ultrastructure of Woody Plants," pp. 271-290, 1965.
Third Party Comments After Patent Owner Response, USPTO Reexamination Control No. 95/001,418, filed by Arch Wood Protection, Inc., Jan. 20, 2011.
Decision on Appeal in Reexamination Control No. 95/001,418, Patent Trial and Appeal Board, Jan. 28, 2013.

\* cited by examiner

Coniferous Wood Anatomy

Bordered Pit

Cross section of micronized copper hydroxide treated wood sprayed with copper indicator Cross section of untreated wood sprayed with copper indicator

MICRONIZED WOOD PRESERVATIVE FORMULATIONS

This application is a continuation-in-part of U.S. patent application Ser. No. 10/821,326, filed on Apr. 9, 2004, now U.S. Pat. No. 7,674,481 which claims the benefit of priority to U.S. Provisional Application Ser. No. 60/461,547, filed Apr. 9, 2003, and U.S. Provisional Application Ser. No. 60/518,994, filed Nov. 11, 2003, the disclosures of which are each incorporated herein by reference. This application is also a continuation-in-part of U.S. patent application Ser. No. 10/970,446, filed on Oct. 21, 2004, which claims the benefit of priority to U.S. Provisional Application Ser. No. 60/568,485, filed May 6, 2004, the disclosures of which are each incorporated herein by reference.

FIELD OF THE INVENTION

The present invention is related generally to the field of wood preservatives and more particularly to a wood preservative composition comprising micronized metal biocides and fungicides.

BACKGROUND OF THE INVENTION

Wood-preserving compositions are well known for preserving wood and other cellulose-based materials, such as paper, particleboard, textiles, rope, etc., against organisms responsible for the destruction of wood, including fungi and insects. Many conventional wood-preserving compositions contain copper-amine complexes. Copper-amine complexes have been used to solubilize copper in aqueous solutions. The copper in such copper-amine complexes is obtained from a variety of copper bearing materials, such as copper scrap, cuprous oxide, copper carbonate, copper hydroxide, a variety of cuprous and cupric salts, and copper bearing ores. The amine in such copper-amine complexes is normally obtained from an aqueous solution of ammonia and ammonium salts, such as ammonium carbonate, and ammonium sulfate, ethanolamines, and the like. For example, U.S. Pat. No. 4,622,248 describes forming copper-amine complexes by dissolving copper (II) oxide [CuO] (also known as cupric oxide) in ammonia in the presence of ammonium bicarbonate.

The disadvantage of using ammonia as a copper solubilizing agent lies in the strong odor of ammonia. Additionally, copper-ammonia preservatives can affect the appearance of the treated wood giving surface residues and undesirable color. In recent years, many amine-containing compounds, such as alkanolamines and aliphatic polyamines, have been used to replace ammonia to formulate water-soluble copper solutions. These compounds were chosen because of their strong complexing ability with copper and because they are essentially odorless. U.S. Pat. No. 4,622,248 discloses a method of preparing copper-amine complexes by dissolving a mixture of copper (II) carbonate [$CuCO_3$] and copper (II) hydroxide [$Cu(OH)_2$] in ethanolamine and water. The complexing amine (i.e., the ligand) and copper (II) ion combine stoichiometrically and thus the weight ratio of reagents will be different for each complexing amine. However, copper-amine based preservatives have higher copper loss due to leaching as compared to traditional copper-based preservatives such as chromated copper arsenate (CCA).

In addition to metal biocides, existing wood preservatives can also contain organic biocides. However, many organic biocides currently in use are not water soluble. Therefore, solubilizing agents, surfactants and wetting agents are often added to either solubilize or form emulsions of the organic biocide to formulate a product that is suitable for the treatment of wood or other cellulose substrates.

However, the solubilizing agents, surfactants, and wetting agents are costly and the use of these products may result in enhanced leaching of the biocides when the treated material comes into contact with moisture. Such enhanced leaching is considered to be the result of the solubilizing agents, surfactants and wetting agents which remain in the wood after treatment. Because these compounds continue to cause leaching of the metal and/or biocide from the treated wood, field performance problems or environmental issues can result.

Despite many efforts to address these deficiencies in existing wood preservatives, there has been an unmet need to produce aqueous metal-based preservatives that are suitable for treating wood and other cellulose-based materials while minimizing the undesirable leaching of metal ions and/or biocide from treated materials when exposed to water. This need is met by the invention disclosed herein.

SUMMARY OF THE INVENTION

The present invention provides micronized compositions for preservation of wood. In one embodiment, the compositions comprise metal or metal compounds as micronized particles.

In another embodiment, the compositions comprise metal or metal compounds and organic biocides. The metal is in an insoluble (micronized form). The metal compounds may be in a soluble form or in a water-insoluble (micronized) form. The organic biocides may be soluble or water insoluble (micronized or emulsified). In the compositions of this embodiment, at least one component (either a metal/metal compound or a biocide) is micronized. Accordingly, in one embodiment, the wood-preservative compositions of the present invention comprise a micronized metal, metal compounds or combinations thereof. In another embodiment, the wood-preservative compositions of the present invention comprise a micronized metal or metal compound and a soluble organic biocide. In another embodiment, the wood-preservative compositions of the present invention comprise a micronized metal or metal compound and a organic biocide emulsion. In another embodiment, the wood-preservative compositions of the present invention comprise micronized metal/metal compounds and micronized organic biocides. In yet another embodiment, the wood-preservative compositions of the present invention comprise a soluble metal compound and micronized organic biocides.

Also provided is a method for using the compositions of the present invention. The method comprises the step of contacting a cellulosic material, such as wood, with a composition of the present invention. When the compositions of the present invention are used for preservation of wood, there is minimal leaching of the metal or metal and the biocide from wood.

The present invention also provides cellulosic materials, including wood, paper, particleboard, textiles, rope, and the like, treated with the compositions of the present invention.

In one embodiment, the preferred metal for wood preserving type applications is copper in the form of a copper compound having a particle size 0.001 microns to 25.0 microns. The copper compound can optionally be mixed with a variety of water soluble and/or water insoluble biocides and then vacuum impregnated, vacuum/pressure or dip impregnated into cellulosic material by standard methods to effectively preserve the material from agents that degrade cellulosic material such as fungi, insects, bacteria etc.

The present invention provides an aqueous wood preservative composition comprising: (a) a micronized inorganic biocide and (b) one or more dispersants. In a preferred embodiment, the micronized inorganic biocide is at least one metal, at least one metal compound or combinations thereof. Preferably, the at least one metal is selected from the group consisting of copper, cobalt, cadmium, nickel, tin, silver, and zinc. More preferably, the at least one metal is copper.

In a preferred embodiment, the at least one metal compound is selected from the group consisting of a compound of copper, cobalt, cadmium, nickel, tin, silver, and zinc. More preferably, the at least one metal compound or complex is a copper compound or complex. Preferably, the copper compound or copper complex is copper hydroxide, copper oxide, copper carbonate, basic copper carbonate, copper oxychloride, copper 8-hydroxyquinolate, copper dimethyldithiocarbamate, copper omadine or copper borate. Most preferably, the copper compound is copper carbonate.

The wood preservative compositions of the present invention preferably comprise a micronized inorganic biocide with a particle size of between 0.001 microns and 25 microns. In another embodiment, the micronized inorganic biocide with a particle size of between 0.001 microns and 10 microns; between 0.05 to 10.0 microns; and between 0.05 to 1.0 microns.

The wood preservative compositions of the present invention preferably comprise a micronized inorganic biocide wherein the micronized inorganic biocide particles have a diameter less than 10 microns. In another embodiment, at least 98, 95, 90, 85, 80, 75, 70, 65, 60, 55, or 50% of the inorganic biocide particles (by weight) have a diameter less than 10 microns. In the compositions of the present invention, at least 3, 5, 10, 15, 20, 25, 30, 35, 40, 45, or 50% of the inorganic biocide particles (by weight) have a diameter of 0.5 microns or greater. In another embodiment, preferably 3 to 25% by weight, more preferably 3 to 10% by weight and still more preferably 3 to 5% by weight of the particles have a diameter of 0.5 microns or greater.

The present invention also provides micronized inorganic biocide compositions in concentrated form comprising between about 1 to 80% of the inorganic biocide by weight of the concentrated composition. In another embodiment, the inorganic biocide comprises 5 to 70% by weight of the concentrated composition. In yet another embodiment, the inorganic biocide comprises 30 to 65% by weight. In yet another embodiment, the compositions of the present invention comprise about 1, 2, 3, 4, 5, 6, 7, 8, 9, 10, 15, 20, 25, 30, 35, 40, 45, 50, 55, 60, 65, 70, 75 or 80% of the inorganic biocide by weight.

The present invention also provides micronized inorganic biocide compositions in concentrated form comprising an inorganic biocide and a dispersant, wherein the dispersant comprises between about 0.1 to 300% by weight of the inorganic biocide. In another embodiment, the dispersant comprises 5 to 150% by weight of the inorganic biocide; In another embodiment, the dispersant comprises 5 to 60%; 10 to 30%; 1 to 80%; 5 to 70%; or 30 to 65% by weight of the inorganic biocide.

In one embodiment, the dispersants used in the wood-preservative compositions of the present invention include, but are not limited to cationic, non-ionic or anionic dispersants, acrylic copolymers, an aqueous solution of copolymers with pigment affinity groups, polycarboxylate ethers, modified polyacrylates, acrylic polymer emulsions, modified acrylic polymers, poly carboxylic acid polymers and their salts, modified poly carboxylic acid polymers and their salts, fatty acid modified polyesters, aliphatic polyethers or modified aliphatic polyethers, polyetherphosphates, solution of polycarboxylate ethers, sodium polyacrylates, sodium polymethacrylates, modified polyether or polyester with pigment affinity groups, fatty acid derivatives, urethane copolymers or modified urethane copolymers, acrylic acid/maleic acid copolymers, polyvinyl pyyrolidones or modified polyvinyl pyrolidones, modified maleic anhydride/styrene copolymers, lignins and the like.

Preferably, the dispersants used in the wood-preservative compositions of the present invention are polymeric dispersants. In one embodiment, the polymeric dispersants contain at least one pigment affinity group capable of binding to a solid particle. In another embodiment, the polymeric dispersants stabilize a solid particle. Preferably, the polymeric dispersants used in the wood-preservative compositions of the present invention are modified polycarboxylate ethers, modified poly carboxylic acid polymers and their salts, solutions of polycarboxylate ethers and modified polyethers or polyesters with pigment affinity groups.

The present invention provides wood-preservative compositions comprising dispersants that function as a wetting agent/dispersing agent. In another embodiment, the dispersants of the present invention disperse the micronized particles of the wood-preservative compositions by reducing the size of particle aggregates. In one embodiment, the dispersants of the present invention disperse the micronized particles of the wood-preservative compositions by binding to the particle surface. In yet another embodiment, the dispersants of the present invention stabilize the micronized particles of the wood-preservative compositions during storage. In yet another embodiment, the dispersants of the present invention prevent flocculation. In one embodiment, the polymeric dispersants are capable of binding a solid particle at least one site on a solid particle surface. The affinity groups of the dispersants of the wood-preservative compositions of the present invention preferably bind a solid particle with high affinity and the polymeric chains of said dispersants preferably extend throughout a solvent system.

The dispersants of the present invention stabilize the micronized particles of the wood-preservative compositions during storage and during repetitive treatments. During repetitive treatment processes, pH change, wood extractives, wood sugars and contaminants from wood surfaces and dirt from air can each affect the function of dispersants and hence dispersed-particle stability.

The present invention also provides wood preservative compositions comprising an inorganic biocide, a dispersant, and further comprising a defoaming agent. Preferably, the defoaming agent is a silicon-containing defoaming agent or a silicon-free defoaming agent. In another embodiment, the defoaming agent is present in an amount between about 0.01 and 10% defoaming agent by weight.

The present invention also provides wood preservative compositions comprising an inorganic biocide, an organic biocide and one or more dispersants. Preferably, the organic biocide is an azole fungicide. In one embodiment, the azole fungicides comprise at least one imidazole or at least one triazole, or both. The present invention also provides wood preservative compositions comprising an inorganic biocide, an organic biocide and one or more dispersants. Preferably, the organic biocide is an azole fungicide. Typical examples of azole compounds include: 1-[[2-(2,4-dichlorophenyl)-1,3-dioxolan-2-yl]methyl]-1H-1,2,4-triazole (azaconazole), 1-[(2RS,4RS:2RS,4SR)-4-bromo-2-(2,4-dichlorophenyl) tetrahydrofurfuryl]-1H-1,2,4-triazole (bromuconazole), (2RS,3RS;2RS,3SR)-2-(4-chlorophenyl)-3-cyclopropyl-1-(1H-1,2,4-triazol-1-yl)butan-2-ol (Cyproconazole), (2RS, 3RS)-1-(2,4-dichlorophenyl)-4,4-dimethyl-2-(1H-1,2,4-triazol-1-yl)pentan-3-ol (diclobutrazol), cis-trans-3-chloro- 4-[4-methyl-2-(1H-1,2,4-triazol-1-ylmethyl)-1,3-dioxolan-2-yl]phenyl 4-chlorophenyl ether (difenoconazole), (E)-(RS)-1-(2,4-dichlorophenyl)-4,4-dimethyl-2-(1H-1,2,4-triazol-1-yl)pent-1-en-3-ol (diniconazole), (E)-(R)-1-(2,4-dichlorophenyl)-4,4-dimethyl-2-(1H-1,2,4-triazol-1-yl) pent-1-en-3-ol (diniconazole-M), (2RS,3SR)-1-[3-(2-chlorophenyl)-2,3-epoxy-2-(4-fluorophenyl)propyl]-1H-1, 2,4-triazole (epoxiconazole), (RS)-1-[2-(2,4-dichlorophenyl)-4-ethyl-1,3-dioxolan-2-ylmethyl]-1H-1,2, 4-triazole (etaconazole), (RS)-4-(4-chlorophenyl)-2-phenyl-2-(1H-1,2,4-triazol-1-ylmethyl)butyronitrile (fenbuconazole), 3-(2,4-dichlorophenyl)-6-fluoro-2-(1H-1, 2,4-triazol-1-yl)quinazolin-4(3H)-one (fluquinconazole), bis (4-fluorophenyl)(methyl)(1H-1,2,4-triazol-1-ylmethyl)silane (flusilazole), (RS)-2,4'-difluoro-α-(1H-1,2,4-triazol-1-ylmethyl) benzhydryl alcohol (flutriafol), (2RS,5RS;2RS, 5SR)-5-(2,4-dichlorophenyl)tetrahydro-5-(1H-1,2,4-triazol-1-ylmethyl)-2-furyl 2,2,2-trifluoroethyl ether (furconazole), (2RS,5RS)-5-(2,4-dichlorophenyl)tetrahydro-5-(1H-1,2,4-triazol-1-ylmethyl)-2-furyl 2,2,2-trifluoroethyl ether(furconazole-cis), (RS)-2-(2,4-dichlorophenyl)-1-(1H-1,2,4-triazol-1-yl)hexan-2-ol (hexaconazole), 4-chlorobenzyl (EZ)-N-(2,4-dichlorophenyl)-2-(1H-1,2,4-triazol-1-yl)thioacetamidate (imibenconazole), (1RS,2SR,5RS;1RS,2SR, 5SR)-2-(4-chlorobenzyl)-5-isopropyl-1-(1H-1,2,4-triazol-1-ylmethyl)cyclopentanol (ipconazole), (1RS,5RS;1RS,5SR)-5-(4-chlorobenzyl)-2,2-dimethyl-1-(1H-1,2,4-triazol-1-ylmethyl)cyclopentanol (metconazole), (RS)-2-(4-chlorophenyl)-2-(1H-1,2,4-triazol-1-ylmethyl)hexanenitrile (myclobutanil), (RS)-1-(2,4-dichloro-β-propylphenethyl)-1H-1,2,4-triazole(penconazole), cis-trans-1-[2-(2,4-dichlorophenyl)-4-propyl-1,3-dioxolan-2-ylmethyl]-1H-1,2,4-triazole (propiconazole), (RS)-2-[2-(1-chlorocyclopropyl)-3-(2-chlorophenyl)-2-hydroxypropyl]-2,4-dihydro-1,2,4-triazole-3-thione (prothioconazole), 3-(2,4-dichlorophenyl)-2-(1H-1,2,4-triazol-1-yl)-quinazolin-4(3H)-one (quinconazole), (RS)-2-(4-fluorophenyl)-1-(1H-1,2,4-triazol-1-yl)-3-(trimethylsilyl)propan-2-ol (simeconazole), (RS)-1-p-chlorophenyl-4,4-dimethyl-3-(1H-1,2,4-triazol-1-ylmethyl)pentan-3-ol (tebuconazole), propiconazole, (RS)-2-(2,4-dichlorophenyl)-3-(1H-1,2,4-triazol-1-yl)propyl 1,1, 2,2-tetrafluoroethyl ether (tetraconazole), (RS)-1-(4-chlorophenoxy)-3,3-dimethyl-1-(1H-1,2,4-triazol-1-yl) butan-2-one (triadimefon), (1RS,2RS;1RS,2SR)-1-(4-chlorophenoxy)-3,3-dimethyl-1-(1H-1,2,4-triazol-1-yl) butan-2-ol (triadimenol), (RS)-(E)-5-(4-chlorobenzylidene)-2,2-dimethyl-1-(1H-1,2,4-triazol-1-ylmethyl)cyclopentanol (triticonazole), (E)-(RS)-1-(4-chlorophenyl)-4,4-dimethyl-2-(1H-1,2,4-triazol-1-yl)pent-1-en-3-ol (uniconazole), (E)-(S)-1-(4-chlorophenyl)-4,4-dimethyl-2-(1H-1,2,4-triazol-1-yl)pent-1-en-3-ol (uniconazole-P), and 2-(2,4-difluorophenyl)-1-(1H-1,2,4-triazole-1-yl)-3-trimethylsilyl-2-propanol. Other azole compounds include: amisulbrom, bitertanol, fluotrimazole, triazbutil, climbazole, clotrimazole, imazalil, oxpoconazole, prochloraz, triflumizole, azaconazole, simeconazole, and hexaconazole. Preferably, the azole fungicide is tebuconazole, propiconazole, simeconazole, cyproconazole or 2-(2,4-difluorophenyl)-1-(1H-1,2,4-triazole-1-yl)-3-trimethylsilyl-2-propanol. More preferably, the azole fungicide is tebuconazole. In one embodiment, the azole fungicide is solubilized, the azole fungicide is emulsified, or the azole fungicide is micronized. In another embodiment, the tebuconazole is solubilized; the tebuconazole is emulsified or the tebuconazole is micronized.

Preferably, the azole fungicide is a triazole compound such as tebuconazole, propiconazole, cyproconazole or 2-(2,4-difluorophenyl)-1-(1H-1,2,4-triazole-1-yl)-3-trimethylsilyl-2-propanol. More preferably, the azole fungicide is tebuconazole. In one embodiment, the azole fungicide is solubilized, the azole fungicide is emulsified, or the azole fungicide is micronized. In another embodiment, the tebuconazole is solubilized; the tebuconazole is emulsified or the tebuconazole is micronized.

The present invention also provides wood preservative compositions comprising an inorganic biocide, an organic biocide and one or more dispersants, wherein the weight ratio of the inorganic biocide to the organic biocide is from about 1000:1 to about 1:100. In another embodiment, the weight ratio of the inorganic biocide to the organic biocide is from about 500:1 to about 1:50. In another embodiment, the weight ratio of the inorganic biocide to the organic biocide is from about 100:1 to about 1:10. In a preferred embodiment, the weight ratio of the inorganic biocide to the organic biocide is from about 50:1 to about 1:1. In a more preferred embodiment, the weight ratio of the inorganic biocide to the organic biocide is from about 25:1 to about 5:1. In another embodiment, the weight ratio of the inorganic biocide to the organic biocide is about 10 to 1 or about 5 to 1.

The present invention also provides wood preservative compositions comprising a micronized copper carbonate, tebuconazole and one or more dispersants, wherein the weight ratio of the copper carbonate to the tebuconazole is about 100 to 1, about 50 to 1 and preferably about 25 to 1. In another embodiment, the weight ratio of the copper carbonate to tebuconazole is about 10 to 1 or about 5 to 1.

The present invention also provides methods for preserving a wood product comprising the step of contacting the wood product with the wood preservative compositions of the present invention. In one embodiment, the treatment of wood is carried out by a process selected from the group consisting of pressure treatment, spraying, dipping and brushing. Preferably, the treatment of wood is carried out by pressure treatment.

The present invention also provides a method of preparing a wood preservative composition comprising the step of mixing a micronized inorganic biocide and an organic biocide. In one embodiment, the micronized inorganic biocide is dispersed in water. In another embodiment, the water further comprises a dispersant. In another embodiment, the organic biocide is dissolved in an organic solvent or emulsified in water.

The present invention also provides a method of preparing a wood preservative composition comprising the step of mixing a micronized inorganic biocide and dispersant. In one embodiment, the methods of the present invention comprise the additional step of mixing an organic biocide with the micronized inorganic biocide and dispersant. In another embodiment, the method of preparing a wood preservative composition comprises the step of milling the composition. In a preferred embodiment, the milling produces a micronized inorganic biocide with a particle size of between about 0.001 microns and 25 microns; between about 0.001 to 10.0 microns between about 0.05 to 10.0 microns; or between 0.05 to 1.0 microns. In another embodiment, at least 98, 95, 90, 85, 80, 75, 70, 65, 60, 55, or 50% of the inorganic biocide particles (by weight) have a diameter less than 10 microns. In the compositions of the present invention, at least 3, 5, 10, 15, 20, 25, 30, 35, 40, 45, or 50% of the inorganic biocide particles (by weight) have a diameter of 0.5 microns or greater. In another embodiment, preferably 3 to 25% by weight, more preferably 3 to 10% by weight and still more preferably 3 to 5% by weight of the particles have a diameter of 0.5 microns or greater.

The present invention also provides wood comprising the wood preservative composition of the present invention, wherein a scanning electron microscopy image of a section of the wood identifies the existence of said micronized particles.

In another embodiment, the wood comprising the wood preservative composition of the present invention is resistant to decay and insect attack as determined by American Wood Preservers' Association Standard (AWPA) Standard E7-01 or AWPA Standard E10-01.

In yet another embodiment, the leaching of copper from the wood of the present invention is less than 50, 20, 10, 5, or, most preferably, 2% of the leaching of copper from wood containing more than 0.001 pcf of non-micronized copper, wherein leaching is measured according to modified American Wood Preservers' Association Standard E11-97.

DETAILED DESCRIPTION OF THE INVENTION

Figure 1A:
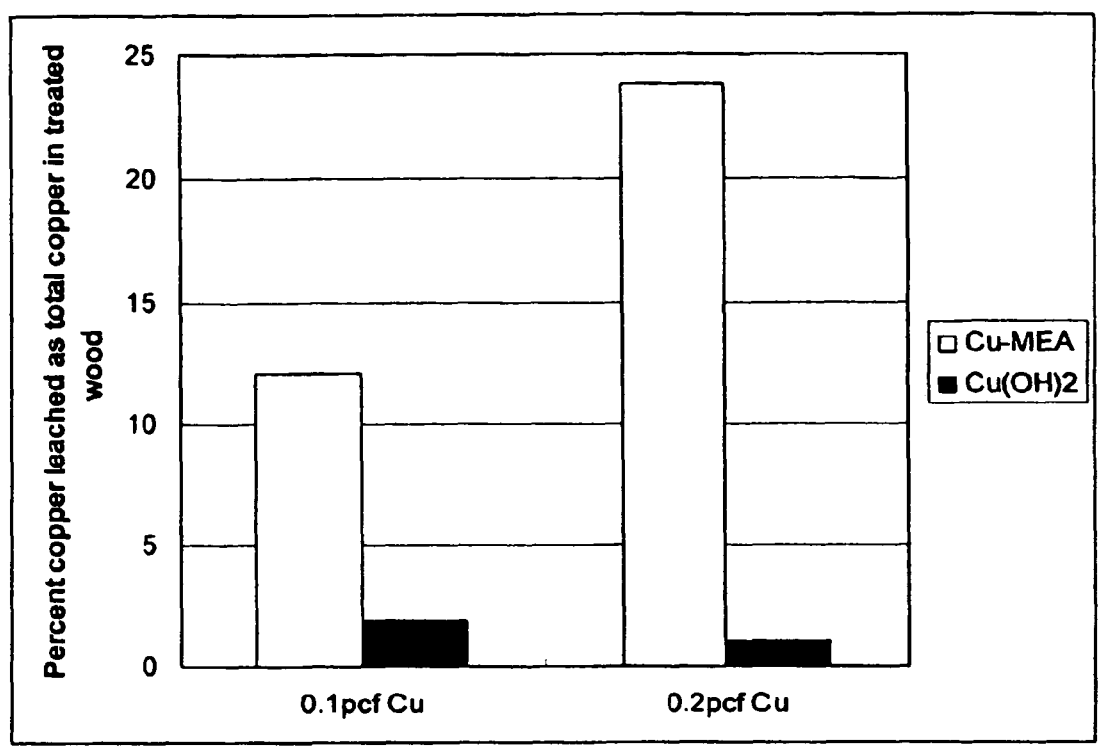
FIG. 1A depicts a comparison of copper leaching from wood treated with copper monoethanolamine (copper mea) vs. micronized copper hydroxide at copper retentions of 0.1 pounds per cubic foot (pcf) and 0.2 pcf according to American Wood Preservers' Association (AWPA) Standard E11-97 "Standard Method of Determining the Leachability of Wood Preservatives".

Unless stated otherwise, such as in the examples, all amounts and numbers used in this specification are intended to be interpreted as modified by the term "about". Likewise, all elements or compounds identified in this specification, unless stated otherwise, are intended to be non-limiting and representative of other elements or compounds generally considered by those skilled in the art as being within the same family of elements or compounds. The term "micronized" as used herein means a particle size in the range of 0.001 to 25 microns. Furthermore, it should be understood that "micronized" does not refer only to particles which have been produced by the finely dividing, such as by mechanical grinding, of materials which are in bulk or other form. Micronized particles can also be formed by other mechanical, chemical or physical methods, such as, for example, formation in solution, with or without a seeding agent, grinding or impinging jet. The term "preservative" as used herein means a composition that renders the material to which it is applied more resistant to insect, fungal and microbial attack than the same material without having the composition applied. The term "particle size" refers to the largest axis of the particle, and in the case of a generally spherical particle, the largest axis is the diameter.

The wood-preservative compositions of the present invention comprise an inorganic biocide comprising a metal, metal compound or combinations thereof and optionally one or more organic biocides. Accordingly, the present invention provides micronized wood preservatives comprising one or more metal or metal compounds with or without one or more organic biocides. When the composition comprises both the metal/metal compounds and the organic biocides, the metal or metal compounds or the organic biocides are present as water insoluble micronized particles. In one embodiment, both the inorganic biocide and the organic biocide are present as micronized particles.

These compositions are used for treatment of cellulosic material, such as wood. The leaching of metal from the treated wood is less for the present compositions than that observed from wood treated with non-micronized compositions.

A preferred metal is copper. Accordingly, in one embodiment, copper or copper compounds are used. The copper or copper compounds such as cuprous oxide (a source of copper (I) ions), cupric oxide (a source of copper (II) ions), copper hydroxide, copper carbonate, basic copper carbonate, copper oxychloride, copper 8-hydroxyquinolate, copper dimethyldithiocarbamate, copper omadine, copper borate, copper residues (copper metal byproducts) or any suitable copper source can be used as micronized particles having a particle size between 0.001 microns to 25 microns. These particles exhibit a relatively low solubility in water.

The copper source can be mixed with water with or without addition of a commercially available rheological additive such as a cellulosic derivative to form a finely dispersed suspension which can be mixed with a biocide to form a preservative system which is suitable to treat and protect wood from agents causing degradation. Other metals or metal compounds as well as transition metals or transition metal compounds (including the lanthanide and actinide series elements) such as tin, zinc, cadmium, silver, nickel, etc. and compounds thereof can be used in place of copper and copper compounds. The resulting metal dispersion or the metal biocide fluid dispersion are suitable for the preservation of wood and other cellulose-based materials.

The organic biocides useful in the present invention can be water soluble as well as water insoluble. Such organic biocides including fungicides, insecticides, moldicides, bactericides, algaecides etc. are well known to those skilled in the art and include azoles, pyrethroid compounds, quaternary ammonium compounds, borate compounds, fluoride compounds and combinations thereof. Some non-limiting examples of water-soluble biocides are quaternary ammonium compounds, such as alkyldimethylbenzylammonium chloride, dimethyldidecylammonium chloride, dimethyldidecylammonium carbonate/bicarbonate and the like. Water insoluble organic biocides are also well known. Some non-limiting example of pyrethroid compounds are bifenthrin, cypermethrin and permethrin.

Other biocides such as insecticides, mold inhibitors, algaecides, bactericides and the like, may also be added to the compositions of the present invention.

The insoluble biocides can be micronized into particles of submicron size ranging from 0.001 micrometers to 25 micrometers using a grinding mill. The particles are dispersed in standard dispersants such as acrylic copolymers, aqueous solution of copolymers with pigment affinity groups, modified polyacrylate, acrylic polymer emulsions, modified lignin and the like.

The compositions of the present invention can be adjusted to the desired pH. For example, the pH can be adjusted to between 2 to 13 by the addition of acids or alkaline components. The acid or alkaline components can be added before, during or after preparation of the micronized particles.

In the compositions of the present invention, at least 98, 95, 90, 85, 80, 75, 70, 65, 60, 55, or 50% of the particles (by weight) have a diameter less than 10 microns. In the compositions of the present invention, at least 3, 5, 10, 15, 20, 25, 30, 35, 40, 45, or 50% by weight have a diameter of 0.5 microns or greater. In another embodiment, preferably 3 to 25% by weight, more preferably 3 to 10% by weight and still more preferably 3 to 5% by weight of the particles have a diameter of 0.5 microns or greater.

In one embodiment, micronized metal or metal compounds such as a copper compound is mixed with an insoluble micronized organic biocide. The metal or metal compound and the insoluble biocide may be micronized separately and then mixed or may be mixed first and then micronized.

In another embodiment, the metal compound is water soluble. Examples of preferred water-soluble metal compounds are copper sulfate, copper acetate and copper nitrate. In this embodiment, an aqueous solution of the copper compound is prepared and then a micronized dispersion of an organic biocide is added to it.

Non-biocidal products such as water repellants (such as wax emulsions), colorants, emulsifying agents, dispersants, stabilizers, UV inhibitors, enhancing agents (such as trialkylamine oxides and alkoxylated diamines) and the like may also be added to the composition disclosed herein to further enhance the performance of the system or the appearance and performance of the resulting treated products. Those skilled in the art will recognize that some of these agents may also have some biocidal properties.

The wood preservative compositions of the present invention may be formulated by several methods. In one embodiment, the wood preservative compositions may be prepared by diluting or mixing a concentrate of a micronized inorganic biocide and an organic biocide with water or another component. In another embodiment, a micronized inorganic biocide is mixed with an organic biocide.

The organic biocides of the wood preservative compositions of the present invention may be provided as a solution in one or more organic solvents, an emulsion in water by emulsifying the compounds with the aid of one or more emulsifiers, or as a dispersion of micronized particles of organic biocide in water.

Non-limiting examples of solvents used for dissolving the organic biocides of the present invention, include dichloromethane, hexane, toluene, alcohols such as methanol, ethanol, and 2-propanol, glycols such as ethylene glycol and propylene glycol, ethers, esters, poly-glycols, poly-ethers, amides, methylene chloride, acetone, chloroform, N,N-dimethyl octanamide, N,N-dimethyl decanamide, N-methyl 2-pyrrolidone, n-(n-octyl)-2-pyrrolidone, and combinations of the above.

In on embodiment, the micronized particles are dispersed by homogenization or high speed agitation or by milling or grinding the organic biocide or by any other chemical or physical means. The micronized particles may be dispersed using dispersants known in the art. Suitable dispersants for use in the wood preservative compositions of the present invention, include cationic, non-ionic or anionic dispersants, acrylic copolymers, an aqueous solution of copolymers with pigment affinity groups, polycarboxylate ethers, modified polyacrylates, acrylic polymer emulsions, modified acrylic polymers, poly carboxylic acid polymers and their salts, modified poly carboxylic acid polymers and their salts, fatty acid modified polyesters, aliphatic polyethers or modified aliphatic polyethers, polyetherphosphates, modified maleic anhydride/styrene copolymers, lignins and the like.

The organic biocides of the wood preservative compositions of the present invention may be provided as an emulsion in water by emulsifying the compounds with the aid of one or more emulsifiers. Emulsifers may be anionic, cationic, or nonionic or combinations thereof. Examples of emulsifers include, but are not limited to, ethoxylated alkylphenols, amines, amides, aryl phenols, fatty esters, fatty acids and derivatives, ethoxylated alcohols and derivatives, sulfonated amines, carboxylated alcohols, alkylphenol ethoxylates, glycol ethers or glycol esters. Additional examples of emulsifers may be found in McCutcheon's Emulsifiers and Detergents, 2005, which is incorporated herein by reference, in its entirety.

For metal or metal compound biocides, the level of dispersant is in the range of from about 0.1 to 180% of the weight of the biocide compounds, with a preferred range of 1 to 80%, a more preferred range of 5 to 60%, and a most preferred range of 10 to 30%. For organic biocides, such as, for example, tebuconazole, cyproconazole, imidacloprid, chlorothalonil, etc, the level of dispersant is in the range of from about 1 to 200% of the weight of the biocide compounds, with a preferred range of 5 to 100%, a more preferred range of 10 to 80%, and a most preferred range of 30 to 70%.

In another embodiment, for metal or metal compound biocides, the level of dispersant is in the range of about 1, 2, 3, 4, 5, 6, 7, 8, 9, 10, 20, 30, 40, 50, 60, 70, 80, 90, 100, 110, 120, 130, 140, 150, 160, 170, 180, 190, or 200% of the weight of the biocide compounds In the present invention, the concentrates of inorganic biocide(s) and organic biocide(s) can be prepared separately and then mix together with water to make a preservative treating composition in wood preservative treating plants. Optionally, a blended concentrate containing inorganic biocide(s) and organic biocide(s) can be prepared and then dilute with water to make a preservative treating composition. The total active ingredients of the preservative treating compositions can vary from 0.001% to 50.0% depending upon the preservative systems, preferably 0.01% to 10.0%, and more preferably from about 0.1% to 3.0%. The compositions of the present invention can be a concentrate or a preparation which is ready to apply to wood. In general, when preparing a biocide concentrate, the total biocide content of the concentrate is in the range of from 1 wt % to 80 wt %, based on weight of composition, and preferably in the range of from 5 to 70 wt %, and more preferably in the range of from 30 to 65 wt %.

In a preferred embodiment, the micronized particles of the present invention are produced by grinding. For example, a slurry comprising a dispersant, a carrier, and a powdered biocide may be ground in the methods of the present invention to a particle size in the range of from 1 micron to 500 microns. In one embodiment, the methods of the present invention optionally contain a defoamer. In one method, the slurry is transferred to a grinding mill that is pre-filled with a grinding media having a size from 0.05 mm to 5 mm, and preferably between 0.1 and 1 mm. The media can be one or more of many commercially-available types, including but not limited to steel shot, carbon-steel shot, stannous-steel shot, chrome-steel shot, ceramic shot (for example, alumina-containing);

zirconium-based shot, such as zirconia, zirconium silicate, zirconium oxide; stabilized zirconia such as stabilized ytz-stabilized zirconia, ceria-stabilized zirconia, stabilized magnesium oxide, stabilized aluminum oxide, etc. The grinding medium preferably occupies 50% to 99% of the grinding chamber volume, with 75 to 95% preferred, and 80 to 90% even more preferred. The bulk density of the grinding media is preferably in the range of from 0.5 kg/l to 10 kg/l, and more preferably in the range of from 2 to 5 kg/l. Agitation speed, which can vary with the size of the grinder, is generally in the range of from 1 to 5000 rpm, but can be higher or lower. A set up which involves a transfer pump which repeatedly cycles the slurry between the mill and a storage tank during grinding is preferred. The transfer pump speed may vary from 1 to 500 rpm. During grinding, defoamer may be added if foaming is observed. During grinding, particle size distribution may be analyzed, and once particle size is within the desired specification, grinding may be stopped.

When wood is treated with micronized wood preservatives formulations disclosed herein, metal leaching is reduced. For example, as shown in FIG. 1A, when wood is treated with Cu-MEA composition the leaching of copper is about 12% and 24% respectively for 0.1 pcf (pounds per cubic feet) copper and 0.2 pcf copper. In contrast when the wood is treated with a micronized composition of the present invention the leaching was only about 2% and 1% respectively for the 0.1 pcf copper and 0.2 pcf copper. Copper leaching was evaluated following the procedures described in American Wood Preservers' Association Standard E11-97.

Wood treated with the micronized preservatives of the present invention exhibits reduced leaching. Accordingly, if wood is treated with micronized copper, copper 30 compounds, copper complexes or combinations thereof such that copper or copper ions are present at a concentration of greater than 0.001 pcf, the leaching of copper from the wood is less that 50% of leaching observed with non-micronized formulations. In another embodiment, at concentrations of copper or copper ions in treated wood greater than 0.001 pcf, the leaching of copper is less than 20% of leaching observed with non-micronized formulations. In yet another embodiment, at concentrations of copper or copper ions in treated wood between 0.001 and 0.05 pcf, the leaching of copper is less than 20% of leaching observed from wood containing greater than 0.001 pcf of non-micronized copper. Preferably, the leaching of copper is less 10%, and more preferably less than 5%, of leaching observed with non-micronized copper formulations when the concentration of copper or copper ions is between 0.001 to 0.5 pcf.

The present invention is not limited to applications which involve micronized particles which have been applied to wood as such. For example, the wood preservative effect of micronized particles can be realized by the formation of such particles in situ. By in situ, it is meant that particle formation takes place on or within the wood. Thus, the benefits of the present invention can be realized if particle formation takes place, for example, within the tracheids of the wood to be preserved. Additionally or instead, particle formation can take place outside of the tracheids, with the subsequent movement of at least some of the particles into the tracheids. Such a movement can be caused by, for example, pressure cycling, such as described in the examples. The micronized particles generally have an average size which is small enough to enable at least partial penetration of wood by particle migration through tracheids and border pits.

It should be understood that unless specifically set forth in conjunction with a method, the term "treatment" as used herein should not be construed as pertaining only to the application of micronized particles to wood which is to be preserved, but also includes in situ formation of micronized formation. Thus, the term "treatment," should generally be construed to encompass all methods as a result of which micronized particles are present in the wood. Thus, the term "treated wood" is only intended to mean wood comprising micronized particles, irrespective of the mode of formation/delivery of the micronized particles.

Figure 1B:
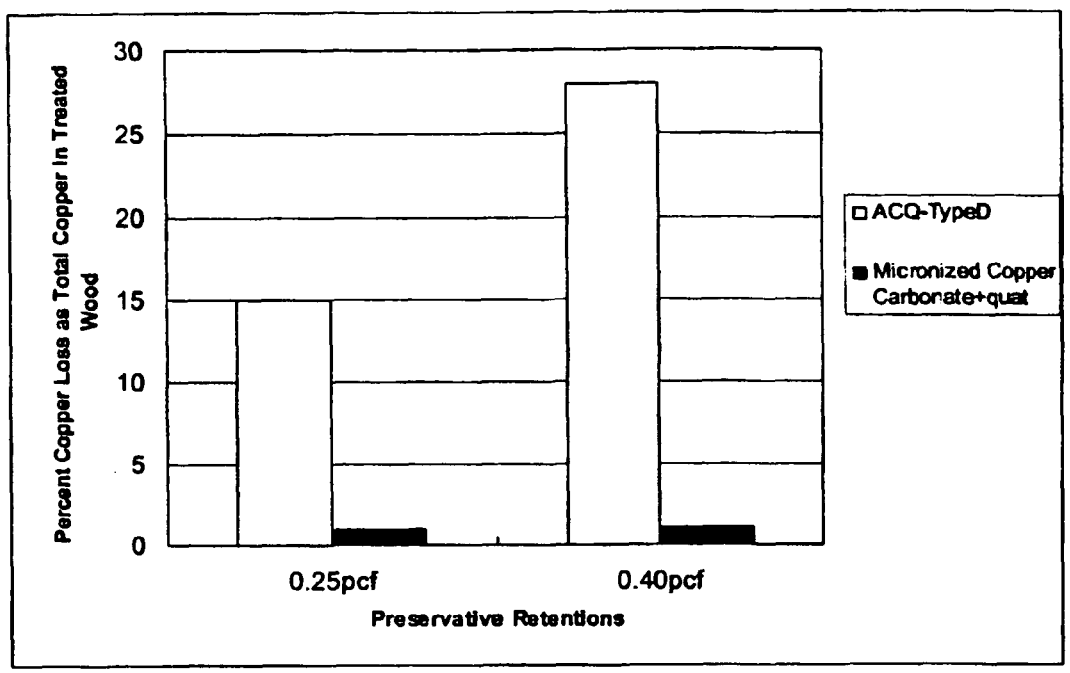
FIG. 1B depicts a comparison of copper leaching from wood treated with a commercial copper based formulation ACQ-Type D and micronized copper carbonate plus dimethyldidecylammonium carbonate/bicarbonate (quat) at preservative retentions of 0.25 pcf and 0.40 pcf. The leaching test was conducted following the procedure described in AWPA Standard E11-97 "Standard Method of Determining the Leachability of Wood Preservatives".

Similarly, FIG. 1B is a comparison of copper leaching from wood treated with a commercial copper based formulation ACQ-Type D and micronized copper carbonate plus dimethyldidecylammonium carbonate/bicarbonate (quat) at preservative retentions of 0.25 pcf and 0.40 pcf. The leaching test was conducted following the procedure described in AWPA Standard E11-97 "Standard Method of Determining the Leachability of Wood Preservatives". It can be seen that wood treated with micronized copper carbonate based formulation demonstrated much greater copper leaching resistance than the wood treated with the commercially available preservative Ammoniacal Copper Quat (ACQ)-Type D.

Figure 2:
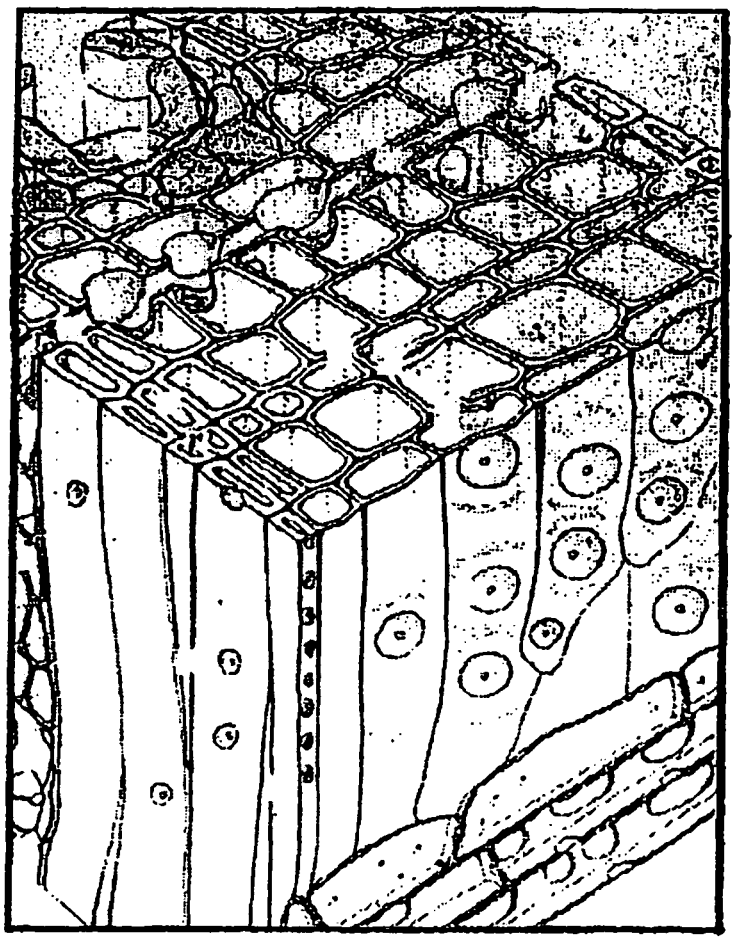
FIG. 2 depicts the anatomy of coniferous wood.

Also important is the penetration of the dispersion formulation into the wood's or other cellulose-based material's cellular structure. If the copper source used in formulating the dispersion formulation disclosed herein has a particle size in excess of 25 microns, the particles may be filtered by the surface of the wood and thus may not be uniformly distributed within the cell and cell wall. As shown in FIG. 2, the primary entry and movement of fluids through wood tissue occurs primarily through the tracheids and border pits. Tracheids have a diameter of about thirty microns. Fluids are transferred between wood cells by means of border pits.

Figure 3:
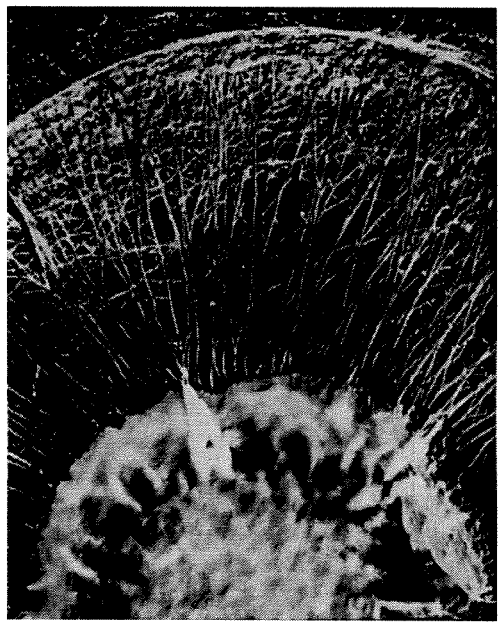
FIG. 3 depicts the border pit structure for coniferous wood.
Figure 3:

The overall diameter of the border pit chambers typically varies from a several microns up to thirty microns while, the diameter of the pit openings (via the microfibrils) typically varies from several hundredths of a micron to several microns. FIG. 3 depicts the border pit structure for coniferous woods.

Figure 4A:
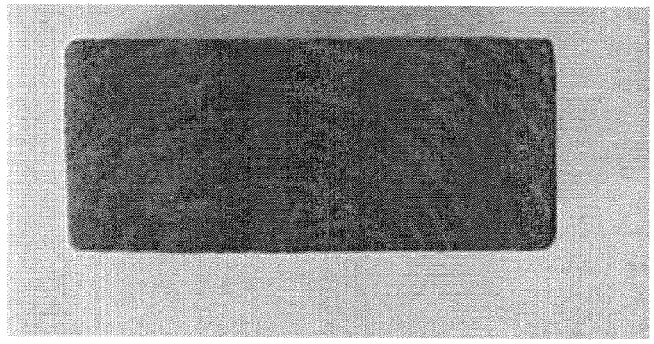
FIG. 4A depicts the uniform copper penetration in wood treated with micronized copper hydroxide according to AWPA Standard A3-00 "Standard Method for Determining Penetration of Preservatives and Fire Retardants".
Figure 4A:
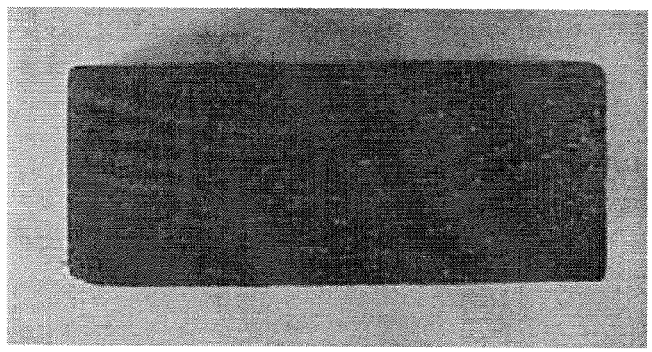
Figure 4B:
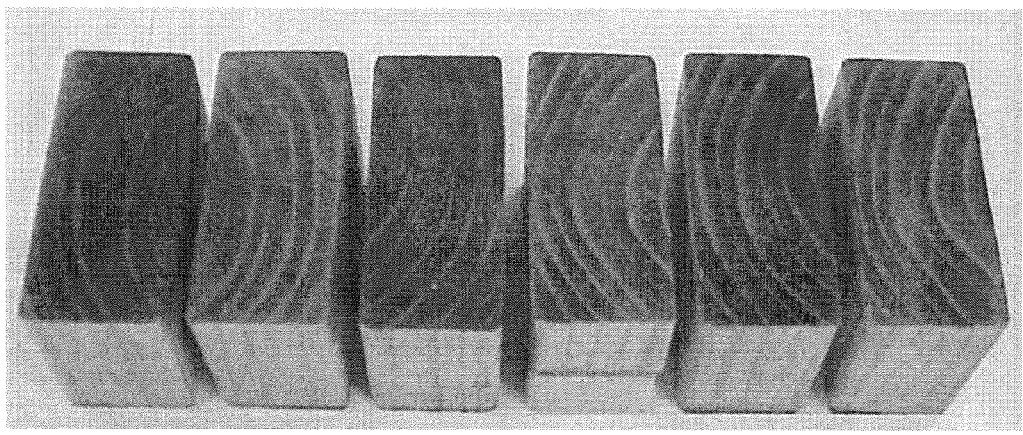
FIG. 4B depicts the uniform copper penetration in wood treated with micronized copper carbonate plus quat. The determination of copper penetration was conducted following the procedures described in AWPA Standard A3-00 "Standard Method for Determining Penetration of Preservatives and Fire Retardants".
Figure 5:
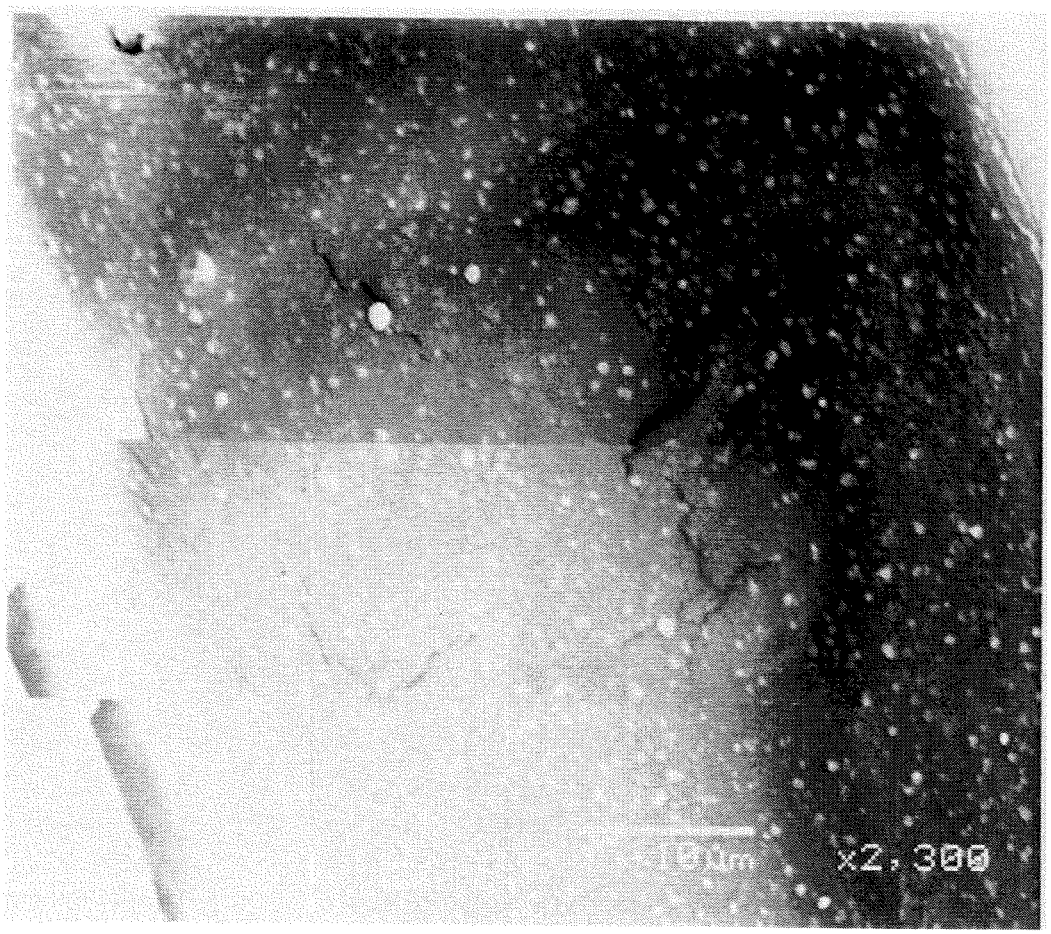
FIG. 5 depicts the uniform particle distribution of cupric oxide through the cells of the wood treated with micronized CuO.

When wood is treated with micronized preservative formulation, if the particle size of the micronized preservative is less than the diameter of the pit openings, a complete penetration and a uniform distribution of micronized preservative in wood is expected. FIG. 4A depicts the complete copper penetration in wood treated with micronized copper hydroxide according to AWPA Standard A3-00 "Standard Method for Determining Penetration of Preservatives and Fire Retardants". A uniform blue was observed indicating the presence of copper. FIG. 4B depicts the complete copper penetration in wood treated with micronized copper carbonate plus quat. Again, a uniform blue color was observed indicating the presence of copper. The determination of copper penetration was conducted following the procedures described in AWPA Standard A3-00 "Standard Method for Determining Penetration of Preservatives and Fire Retardants". FIG. 5 depicts the uniform particle distribution of cupric oxide through the cells of the wood treated with micronized CuO through the observation of Scanning Electron Microscope (SEM). The particles were confirmed to be copper compounds by the use of SEM-Energy Dispersed X-ray Analysis (EDXA).

Particle size of the metal, metal compounds or organic biocide used in the dispersion formulation disclosed herein typically does not exceed 30 microns or the metal and or organic biocide used in conjunction with the metal tends to be filtered by the surface of the wood thus not attaining a desired penetration and fluid flow through the wood tissue. In one embodiment particle size of the micronized particles used in the dispersion formulation disclosed herein can be between 0.001-10 microns. In another embodiment, the particle size is between 0.001 to 1.0 micron. In another embodiment, the particle size is between 0.05 to 10.0 microns. If a more uniform penetration is desired, particle size of the metal/metal compounds or the organic biocide used in the dispersion formulation disclosed herein can be between 0.05-1.0 microns.

The present invention also provides a method for preservation of wood. In one embodiment, the method comprises the steps of treating wood with a composition (treating fluid) comprising a dispersion of water insoluble micronized metal and/or metal compounds. In another embodiment, wood is treated with a composition comprising a dispersion of micronized metal and/or metal compounds and organic biocides, wherein the organic biocides are soluble or present as water insoluble micronized particles. The size of the micronized particles for the metal/metal compounds and organic biocide is between 0.001 to 25 microns, preferably between 0.001 to 10 microns, more preferably between 0.05 to 10 micron and even more preferably between 0.05 to 1.0 microns. In another embodiment, the wood is treated with a composition comprising soluble metal compounds and micronized organic biocides.

The treating fluid may be applied to wood by dipping, soaking, spraying, brushing, or any other means well known in the art. In a preferred embodiment, vacuum and/or pressure techniques are used to impregnate the wood in accord with this invention including the standard processes, such as the "Empty Cell" process, the "Modified Full Cell" process and the "Full Cell" process, and any other vacuum and/or pressure processes which are well known to those skilled in the art.

The standard processes are defined as described in AWPA Standard C1-03 "All Timber Products—Preservative Treatment by Pressure Processes". In the "Empty Cell" process, prior to the introduction of preservative, materials are subjected to atmospheric air pressure (Lowry) or to higher air pressures (Rueping) of the necessary intensity and duration. In the "Modified Full Cell", prior to introduction of preservative, materials are subjected to a vacuum of less than 77 kPa (22 inch Hg) (sea level equivalent). A final vacuum of not less than 77 kPa (22 inch Hg) (sea level equivalent) shall be used. In the "Full Cell Process", prior to introduction of preservative or during any period of condition prior to treatment, materials are subjected to a vacuum of not less than 77 kPa (22 inch Hg). A final vacuum of not less than 77 kPa (22 inch Hg) is used.

EXAMPLES

The following examples are provided to further describe certain embodiments of the invention but are in no way meant to limit the scope of the invention. Examples 1 through 5 demonstrate the formulation of the concentrated dispersions of copper compounds and the concentrated dispersions of copper compounds comprising various organic biocides. Examples 6 through 14 demonstrate the preparation of treating fluids using concentrated dispersions for the treatment of wood.

Example 1

500 g of copper hydroxide were added to a container containing 1091.7 grams of water and 75.0 grams of commercially available dispersants/wetting agents. The mixture was mechanically stirred for 5 minutes and then placed in a grinding mill. The sample was ground for about 30 minutes, and a stable dispersion containing about 30% copper hydroxide was obtained. The particle size of the copper hydroxide dispersion was analyzed by Horiba LA-910 Particle Size Distribution Analyzer (PSDA). The average particle size was 0.195 micrometers (um) with a distribution range of 0.04 um to 1.5 um.

Example 2

1000 grams of basic copper carbonate was mixed with 2158.3 grams of water and 175.0 grams of commercially available wetting agents/dispersants. The mixture was mechanically stirred for 10 minutes. The mixture was then placed in a grinding mill and ground for about 20 minutes. A stable dispersion was obtained with an average particle size of 0.199 micrometers.

Example 3

1000 grams of basic copper carbonate and 20 grams of tebuconazole were mixed with 3780 grams of water and 200 grams of wetting agents/dispersants. The mixture was mechanically stirred for about 10 minutes. The mixture was then placed in a grinding mill and ground for about 30 minutes. A stable dispersion containing 25% basic copper carbonate and 0.5% tebuconazole was obtained with an average particle size of 0.200 micrometers.

Example 4

300 grams of copper 8-hydroxyquinolate (Cu-8) were mixed with 855 grams of water and 45 grams of dispersants. The mixture was mechanically mixed for about 5 minutes and placed in a grinding mill. The mixture was ground for about 30 minutes and a stable dispersion containing 25% Cu-8 was obtained with an average particle size of 0.282 micrometers.

Example 5

A stable cupric oxide (CuO) dispersion containing about 30% CuO was supplied by Nanophase Technologies, Inc. The average particle size was about 0.1 micrometers. This can be mixed with organic soluble or micronized biocides.

Example 6

38.5 g of cupric hydroxide dispersion from Example 1 was mixed with 7.5 g of N,N-dimethyl-1-dodecylamine-N-oxide (AO) and 2954.0 g of water to produce a preservative treating fluid containing 0.385% cupric hydroxide and 0.25% AO. The fluid was then used to treat 2"×4"×10" samples of southern pine sapwood, and sealed with epoxy resin, using an initial vacuum of 28" Hg for 15 minutes, followed by a pressure cycle of 135 psi for 25 minutes and a final vacuum of 27" Hg for 10 minutes. The resulting treated wood was weighed and found to have doubled its weight. The treated sample was cut and the cross sections sprayed with a copper indicator to determine copper penetration following the procedure described in American Wood Preservers' Association Standard A3-00, and the blue color indicates the presence of copper. The sample was found to have 100% uniform distribution of copper throughout the cross section as in FIG. 4A. As a comparison, FIG. 4A also showed the cross section of untreated wood.

Example 7

50.0 g CuO dispersion from Example 5 were mixed with 2942.5 g of water and 7.5 g of didecyldimethylammonium chloride. The product was mixed until uniformly dispersed and the treating solution containing the following compositions was obtained: 2 Components Percent Cupric Oxide 0.50 Didecyldimethylammonium Chloride 0.25

A southern pine stake measuring 1.5"×3.5"×10" was placed in a laboratory retort with a vacuum of 27" Hg for 15 minutes. The treating solution was then pumped into the retort and the retort pressurized to 130 psi for 30 minutes. The solution was drained from the retort and the test stake weighed. Based on the weight pickup, the test stake doubled its weight and showed uniform penetration of the cupric oxide throughout the wood cross section. A sample taken from the center portion of the treated wood was submitted for scanning electron microscopy (SEM) analysis, and the SEM result indicated the uniform particle distribution in wood as shown in FIG. 5.

Example 8

4000 g of treating fluid containing 0.31% of cupric oxide and 0.16% didecyldimethylammonium carbonate were prepared by mixing CuO dispersion from Example 5 and didecyldimethylammonium carbonate. The fluid was used to treat 2"×4"×10" southern pine samples by placing the samples in a chamber and drawing a 27" Hg vacuum for 10 minutes. The treating fluid was then drawn into the chamber and allowed to stay in contact with the wood cubes for 15 minutes. The fluid was pumped from the chamber and the resulting wood had more than doubled its weight. Cross sections of the cubes showed 100% copper penetration.

Example 9

A preservative treating formulation was prepared by adding 0.15 kg of copper carbonate dispersion from Example 2 to 0.025 kg of N,N-dimethyl-1-hexadecylamine-N-oxide and 4.825 kg of water. This fluid was allowed to mix until a homogenous fluid was prepared. This fluid was used to treat southern pine test stakes measuring 0.156×1.5×1-0.0 inches (4×38×254 mm) by the full-cell process. The resulting stakes showed a uniform distribution of copper throughout the wood cells. The treated test stakes were installed in the field to evaluate the field performance of the preservative following the procedure described in AWPA Standard E7-01 "Standard Method of Evaluating Wood Preservatives by Field Tests with Stakes". The test results indicated that the treated stakes were resistant to decay and insect attack. The fluid was also used to treat southern pine wood cube blocks measuring ¾"×¾"×¾" (19 mm×19 mm×19 mm). The treated cubes were exposed to several test fungi to evaluate the bio-efficacy of the preservative formulation following the procedure described in AWPA Standard E10-01 "Standard Method of Testing Wood Preservatives by Laboratory Soil-Block Cultures". Upon the completion of the soil-block test, the cubes were found to have less than 2.0% weight loss, indicating essentially no fungal attack to the treated cubes. In comparison, untreated wood cubes had approximately 50% weight loss after being exposed to the test fungi. The soil block test results indicated wood treated the above preservative formulation was resistant to fungal attack.

Example 10

A preservative treating composition was prepared by adding 0.1 kg of dispersion from Example 3 to 4.9 kg of water. The resulting fluid contained 0.50% copper carbonate and 0.01% tebuconazole. This fluid was then used to treat full-size lumber using the full-cell process wherein the wood is initially placed under a vacuum of 30" Hg for 30 minutes, followed by the addition of the treating solution. The system was then pressurized for 30 minutes at 110 psi. A final vacuum of 28" Hg for 30 minutes was applied to the wood to remove residual liquid. The wood was found to contain a uniform distribution of copper throughout the cross sections and is resistant to fungal and insect attack.

Example 11

54 g of dispersion from Example 3 and 7.5 g of N,N-dimethyl-1-hexadecylamine-N-oxide (AO) were mixed with 2938.5 grams of water to obtain a preservative treating fluid containing 0.45% carbonate, 0.009% tebuconazole and 0.25% AO. The resulting fluid was used to treat red pine lumber using a modified full-cell process. The resulting stakes were air-dried and found to a uniform distribution of copper throughout the cross sections and were resistant to fungal and insect attack.

Example 12

A preservative treating fluid was prepared by adding 16.0 g of Cu 8-hydroxyquinolate (Cu-8) dispersion from Example 4 to 3984.0 g of water. The resulting fluid contained 0.1% Cu-8. The fluid was used to treat southern pine lumber using a full cell process. The treated stakes were oven dried and found to contain a uniform distribution of particles throughout the cross sections and were resistant to fungal and insect attack.

Example 13

A preservative treating fluid was prepared by mixing 175 g concentrated dispersion containing 20% copper carbonate and 0.5% cyproconazole with 3325.0 g water. The resulting solution contained 1.0% copper carbonate and 0.025% cyproconazole and was used to treat southern pine lumber using a full cell process. The treated stakes were oven dried and found to contain a uniform distribution of copper and cyproconazole throughout the cross sections and were resistant to fungal and insect attack.

Example 14

A preservative treating fluid can be prepared by mixing copper sulfate solution and micronized cyproconazole at a concentration of 0.25% Cu and 0.01% cyproconazole. The resulting fluid can be used to treat lumber using a full cell process. The treated sample can be air-dried for two weeks and tested for resistance to fungal and termite attack.

Although specific embodiments have been described herein, those skilled in the art will recognize that routine modifications can be made without departing from the spirit of the invention.

Example 15

Two wood-treatment compositions were compared in an accelerated laboratory test using the copper-tolerant fungi *C. puteana* and *P. placenta*. The testing was performed following the procedure described in American Wood Preservers' Association (AWPA) Standard E10-01: "Standard Method of Testing Wood Preservatives by Laboratory Soil Block Cultures". The results of this comparison are presented in Table 1.

TABLE 1

Accelerated Laboratory Soil Block Test of Micronized Copper Formulations against Copper Tolerant Fungi

| Treatment | Retention (kg/m3) | Weight Loss, % C. puteana | Weight Loss, % P. placenta |
|---|---|---|---|
| Untreated Control | 0.0 | 47.6 | 53.4 |
| Micronized Copper Carbonate | 0.8 Cu | 49.2 | 37.8 |
| | 1.6 Cu | 46.6 | 33.2 |
| | 2.4 Cu | 51.6 | 27.3 |
| | 3.2 Cu | 46.1 | 39.5 |
| Micronized Copper Carbonate + Tebuconazole | 0.8 Cu + 0.032 Tebuconazole | 2.7 | 0.0 |
| | 1.6 Cu + 0.064 Tebuconazole | 0.0 | 0.0 |
| | 2.4 Cu + 0.096 Tebuconazole | 0.0 | 0.0 |
| | 3.2 Cu + 0.128 Tebuconazole | 0.0 | 0.0 |

Example 16

Two wood-treatment compositions were compared in a 12-month field study. The field performance test was evaluated following the procedure described in American Wood Preservers' Association (AWPA) Standard E7-01: "Standard Method of Evaluating Wood Preservatives by Field Tests with Stakes". The results of this comparison are presented in Table 2. The numerical decay rating system is described in Table 3.

TABLE 2

Average Decay Ratings of a Micronized Copper/Tebuconazole Preservative Treated Wood Stakes (4 × 38 × 254 mm) Installed in Gainesville, Florida for 12 months

| Treatment | Retention (kg/m3) | Decay Rating |
|---|---|---|
| Untreated Control | 0.0 | 3.8 |
| Tebuconazole | 0.32 Tebuconazole | 8.2 |
| | 0.48 Tebuconazole | 5.8 |
| | 0.64 Tebuconaozle | 8.7 |
| Micronized Copper Carbonate + Tebuconazole | 0.8 Cu + 0.032 Tebuconazole | 10.0 |
| | 1.6 Cu + 0.064 Tebuconazole | 10.0 |
| | 2.4 Cu + 0.096 Tebuconazole | 10.0 |
| | 3.2 Cu + 0.128 Tebuconazole | 10.0 |

TABLE 3

Description of numerical decay ratings.

| Decay Rating | Description |
|---|---|
| 10 | Sound (suspicion of decay permitted) |
| 9 | Trace decay to 3% of cross section |
| 8 | Decay from 3 to 10% of cross section |
| 7 | Decay from 10 to 30% of cross section |
| 6 | Decay from 30 to 50% of cross section |
| 4 | Decay from 50 to 75% of cross section |
| 0 | Failure |

We claim:

1. A method for preserving a wood product comprising vacuum and/or pressure treating the wood product with a wood preservative composition comprising: (a) a dispersion in water of particles of a copper compound with a particle size of between 0.001 and 25 microns and optionally (b) an organic biocide;
    so that the particles of the copper compound are distributed throughout the wood product.

2. The method of claim 1, wherein the wood preservative composition comprises an organic biocide.

3. The method of claim 2, wherein the organic biocide is selected from the group consisting of an azole compound, pyrethroid compound, quaternary ammonium compound, borate compound and fluoride compound.

4. The method of claim 3, wherein the azole compound is cyproconazole or tebuconazole.

5. The method of claim 3, wherein the pyrethroid compound is bifenthrin or cypermethrin.

6. The method of claim 3, wherein the quaternary ammonium compound is alkyldimethylbenzylammonium chloride, dimethyldidecylammonium chloride, dimethyldidecylammonium carbonate, or dimethyldidecylammonium bicarbonate.

7. The method of claim 1, wherein the copper compound is uniformly distributed throughout a cross-section of the wood product.

8. The method of claim 7, wherein the wood product is coniferous wood.

9. The method of claim 8, wherein the coniferous wood is southern pine.

10. The method of claim 1, wherein the wood product is lumber.

11. The method of claim 1, wherein the treatment renders the wood product resistant to fungal decay.

12. The method of claim 1, wherein the copper compound is selected from the group consisting of copper hydroxide, cupric oxide, cuprous oxide, copper carbonate, basic copper carbonate, copper oxychloride, copper 8-hydroxyquinolate, copper dimethyldithiocarbamate, copper omadine and copper borate.

13. The method of claim 1, wherein the copper compound is milled.

14. The method of claim 1, wherein the wood preservative composition comprises a dispersion in water of a copper compound with a particle size of between 0.05 and 1 microns.

* * * * *